(12) United States Patent
Mayer et al.

(10) Patent No.: US 12,064,152 B2
(45) Date of Patent: Aug. 20, 2024

(54) IMPLANT FIXATION

(71) Applicant: Woodwelding AG, Stansstad (CH)

(72) Inventors: Jörg Mayer, Niederlenz (CH); Andrea Müller, Winterthur (CH); Andrè Schwery, Bern (CH)

(73) Assignee: WOODWELDING AG, Stansstad (CH)

( * ) Notice: Subject to any disclaimer, the term of this patent is extended or adjusted under 35 U.S.C. 154(b) by 1079 days.

(21) Appl. No.: 16/960,418

(22) PCT Filed: Jan. 8, 2019

(86) PCT No.: PCT/EP2019/050352
§ 371 (c)(1),
(2) Date: Jul. 7, 2020

(87) PCT Pub. No.: WO2019/137921
PCT Pub. Date: Jul. 18, 2019

(65) Prior Publication Data
US 2020/0367948 A1 Nov. 26, 2020

(30) Foreign Application Priority Data

Jan. 9, 2018 (CH) .................................. 00016/18
May 23, 2018 (CH) .................................. 00660/18

(51) Int. Cl.
*A61B 17/80* (2006.01)
*A61B 17/00* (2006.01)
*A61B 17/70* (2006.01)

(52) U.S. Cl.
CPC .... *A61B 17/8042* (2013.01); *A61B 17/00491* (2013.01); *A61B 17/7059* (2013.01);
(Continued)

(58) Field of Classification Search
CPC . A61B 17/80; A61B 17/8042; A61B 17/8047; A61B 17/7059
See application file for complete search history.

(56) References Cited

U.S. PATENT DOCUMENTS

2007/0270833 A1* 11/2007 Bonutti .................. G06F 21/10
606/28
2009/0018590 A1* 1/2009 Dorawa ............... A61B 17/864
606/301
(Continued)

FOREIGN PATENT DOCUMENTS

WO  02/069817    9/2002
WO  2004/017857  3/2004
(Continued)

*Primary Examiner* — Si Ming Ku
(74) *Attorney, Agent, or Firm* — Rankin, Hill & Clark LLP

(57) ABSTRACT

A modular implant system, such as a spinal implant system, having an implant part, for example a (spinal) plate, and at least one fastener, wherein the implant part has a fastener receiving opening. The system also includes thermoplastic material, the thermoplastic material being equipped for being liquefied by mechanical vibration, especially ultrasonic vibration energy. The fastener receiving opening and the fastener can be shaped so that the fastener can be inserted relative to the implant part at a variable angle. The fastener, the plate and the thermoplastic material are equipped for the thermoplastic material, after re-solidification, to secure the fastener against at least one of an axial (back-out) movement of the fastener, a rotation of the fastener relative to the implant part, a variation of the angle of the fastener relative to the implant part.

35 Claims, 12 Drawing Sheets

(52) U.S. Cl.
CPC .... *A61B 17/8047* (2013.01); *A61B 2017/005* (2013.01); *A61B 2017/00955* (2013.01)

(56) References Cited

U.S. PATENT DOCUMENTS

| | | |
|---|---|---|
| 2009/0198284 A1 | 8/2009 | Henry |
| 2010/0023057 A1* | 1/2010 | Aeschlimann ........ A61F 2/4405 606/62 |
| 2010/0114097 A1* | 5/2010 | Siravo ................ A61B 17/8047 606/62 |
| 2016/0022334 A1 | 1/2016 | Bonutti et al. |
| 2016/0106483 A1 | 4/2016 | Mayer et al. |
| 2017/0119448 A1 | 5/2017 | Mayer et al. |

FOREIGN PATENT DOCUMENTS

| | | |
|---|---|---|
| WO | 2010/096942 | 9/2009 |
| WO | 2009/117387 | 10/2009 |
| WO | 2011/054124 | 5/2011 |

\* cited by examiner

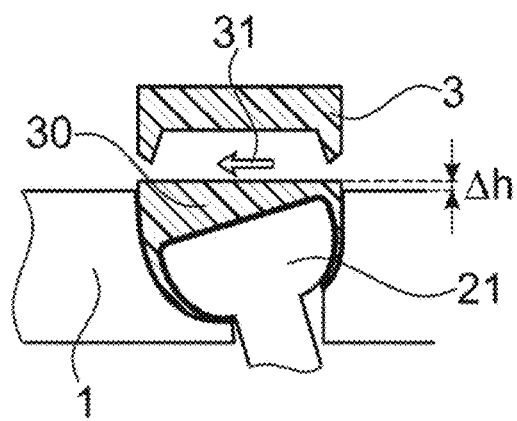
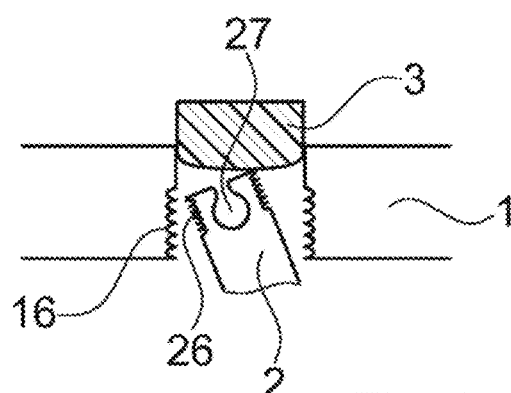
Fig. 8  Fig. 9
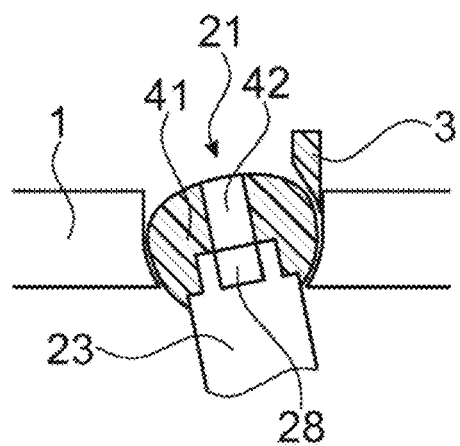
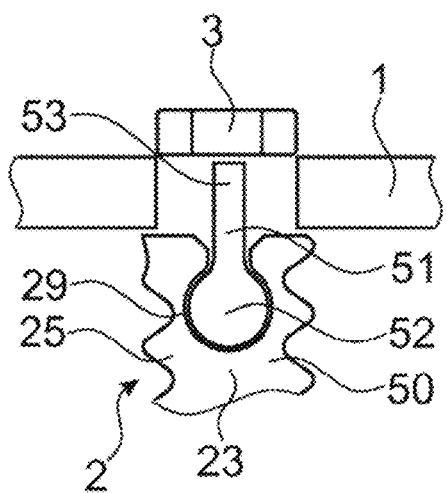
Fig. 10  Fig. 11
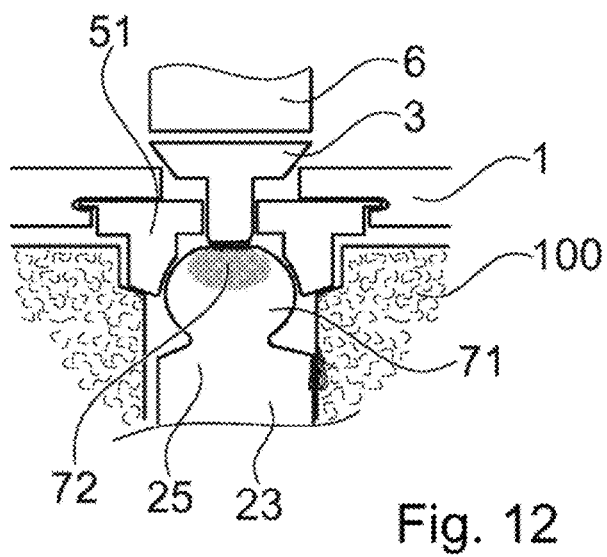
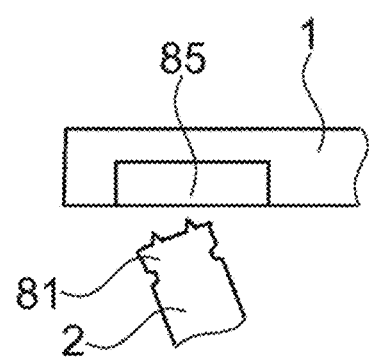
Fig. 12  Fig. 13

IMPLANT FIXATION

BACKGROUND OF THE INVENTION

Field of the Invention

The invention is in the field of implant systems, in particular modular implant systems, such as modular prostheses, intramedullary nails and osteosynthesis systems, for example spinal implant systems.

Description of Related Art

Usually, an implant part of a modular implant system is fastened relative to another implant part of the modular implant system and/or to bone tissue by a fastener.

For example, spinal implant systems include systems in which different vertebrae are stabilized with respect to each other by a fixation element, in particular a plate.

Usually, spinal plates are fastened relative to the vertebrae by means of fasteners, such as surgical screws. Similarly, orthopaedic plates or rods, for human or veterinary applications, are affixed to bone by orthopaedic screws and implant parts of modular prostheses, for example modular intramedullary nail for femoral neck fractures or proximal humerus fractures or modular hip or humerus prostheses, are affixed relative to each other by implant screws.

Fixation of the fastener relative to an implant part, such as the plate, may need to address the following requirements:
  The prevention of a backout situation: once the fastener is inserted, it must be fixed relative to the implant part, for example the plate, even if the anchoring should fail at some later stage, so that it is ascertained that there can never be any damage to surrounding tissue caused by a fastener backing out towards proximally. Backout especially is a potential problem if the fastener is a screw, for example due to accumulated micro-movements.
  Minimal profile: the fastener must not stick out too much towards proximally. This is especially, but not only, very critical in case the implant part is an anterior cervical plate, because of the location of the immediately adjacent oesophagus.
  Angular stability. Often, the angle between the fastener on the one hand and the implant part, for example a spinal plate plane, on the other hand is not fixed or predefined, but is chosen by the surgeon based on the clinical situation. The angle between the fastener and the implant part, for example the plate, for many clinical situations may, however, need to be fixed after implantation.

US 2009/0198284 discloses a hybrid plate system and method with a polymer component between the respective fastener (pin) and the bone plate. The polymer is melted through the application of ultrasonic energy so that the re-solidified polymer creates a bond between the pin and the bone plate.

WO 2009/117837 discloses a surgical device for osteosynthesis, in which a heating element is used to liquefy a polymer that bonds a pin-like fastener to a fixation element.

SUMMARY OF THE INVENTION

It would be desirable to have an implant system, in particular a modular implant system or an osteosynthesis system, such as a spinal implant system to be secured to human spine, which system overcomes drawbacks of prior art implant systems. It is a further object of the present invention to provide a surgical method of securing an implant system to bone tissue, for example a spinal system to a human spine, and/or securing implant parts of the implant system relative to each other, the method overcoming disadvantages of the prior art.

The implant system includes an implant part and at least one fastener, wherein the implant part has, for the fastener, for example for every fastener, a fastener receiving opening. The system further includes thermoplastic material, wherein the thermoplastic material is equipped for being liquefied by ultrasonic vibration. The fastener, the implant part and the thermoplastic material are equipped for the thermoplastic material, after re-solidification, to secure the fastener against at least one of an axial (back-out) movement of the fastener, a rotation of the fastener relative to the implant part, a variation of the angle of the fastener relative to the implant part. Further, the thermoplastic material is decoupled vibrationally from the implant part and the at least one fastener.

"Decoupled vibrationally" means that the thermoplastic material, for example being part of a securing element (sometimes called backout prevention element) as described in detail below or of another element of the implant system, for example of the implant part or of the fastener, can be set in vibration, in particular ultrasonic vibration, without setting the implant part and the at least one fastener or—as the case may be—any other element of the implant system in (ultrasonic) vibration.

The thermoplastic material is thus provided as an initially separate element, namely securing element, and/or as an element that is initially attached to the implant part, fastener or other element but is separable therefrom to be a separate element. Such separation is especially possible by applying a pressing or twisting force on the thermoplastic material relative to the implant part/fastener/other element and/or by an onset of vibration acting onto the thermoplastic material.

The thermoplastic material, for example being part of the securing element, can be arranged or arrangeable such that the ultrasonic vibrations can be coupled directly into the thermoplastic material, for example—as the case may be—directly into the securing element. For example, the thermoplastic material (for example of the securing element) can be arranged or arrangeable such that a sonotrode can be brought in direct contact with the thermoplastic material.

In embodiments, the thermoplastic material, for example being part of the securing element, can be attached to the fastener, the implant part or another element of the implant system. However, at least one of the following applies in such embodiments:
  The attachment between thermoplastic material (the securing element, as the case may be) and fastener, implant part or the other element of the implant system breaks as soon as ultrasonic vibration is coupled in;
  The thermoplastic material belongs to a securing element attached to the fastener, implant part or other element by a connection via a connection forming a predetermined breaking point, wherein such connection breaks by application of a directed force.

In any case, the implant system may be equipped for mechanical vibration to be coupled into the thermoplastic material (especially securing element) while the implant part, fastener and/or other element(s) does/do not vibrate. For example, the mechanical vibration may be coupled into the thermoplastic material while the implant part, fastener and/or other element(s) is/are coupled to the patient's body.

In any embodiment, the implant part can be a fixation element, in particular a fixation element used in osteosynthesis or in spine stabilization.

The fixation element can include a plate, in particular a fixation plate, such as a spinal plate, for example an anterior cervical plate, or a compression plate, or the fixation element can include a fixation rod, such as an intramedullary rod, for example.

In any embodiment, the implant part can be a plate, in particular a fixation plate such as a spinal plate, for example an anterior cervical plate, or a compression plate, being shaped to be placed against human or animal bone tissue or the fixation element can be a rod, in particular a fixation rod, such as intramedullary rod.

In an embodiment, the implant part is a first implant part and the implant system includes a second implant part. In such an embodiment, the first implant part, the second implant part and the fastener are equipped for the fastener to fix the relative position of the first and second implant part.

For example, the fastener can be equipped to clamp the first implant part to the second implant part and/or the second implant part to the first implant part. A fixation rod that is clamped by the fastener to a rod holder such as the tulip of a pedicle screw is an example for this embodiment. In this example, the rod holder can be equalized with the first implant part, the fixation rod can be equalized with the second implant part and the fastener can be realized as a setscrew.

The fastener can be equipped to clamp together the first and second implant parts.

For example, the fastener and at least one of the first implant part and the second implant part can be equipped for the fastener to be anchored in at least one of the first implant part and the second implant part. For example, first and second implant parts can be parts of a modular prosthesis, such as a modular humerus prosthesis or a modular hip prosthesis. In this example, the fastener can be realized as a screw, for example a tensioning screw, designed to fix the first implant part relative to the second implant part.

For example, the first and the second implant parts can be parts of an intramedullary nail.

In an embodiment, the implant system can be designed in a manner that the fastener can be moved relative to the implant part, wherein there is a relative arrangement of fastener and implant part in which the fastener generates a clamping force to the implant part.

For example, the implant part and the fastener can be designed for the fastener to clamp the implant part between the fastener and another element of the implant system, for example the second implant part, or between the fastener and bone tissue by the relative movement of the fastener and implant part and—as the case may be—during implantation of the implant system.

In all embodiments including a fastener equipped and/or designed for clamping the implant part, the implant system can be designed for the thermoplastic material (the securing element, as the case may be) to prevent after re-solidification a relative movement of fastener and implant part that reduces the clamping force. The thermoplastic material can prevent the relative movement in a direct manner or in an indirect manner, for example by fixing the securing element, wherein the portion of the securing element that finally prevents said movement is not made from thermoplastic material and/or does not liquefy at the energies applies.

Accordingly in all embodiments including a fastener equipped and/or designed for fixing the implant part, the implant system can be designed for the thermoplastic material (the securing element, as the case may be) to prevent a relative movement of fastener and implant part that loosens the fixation established by the fastener.

In particular, the thermoplastic material (the securing element, as the case may be) can be arrangeable to prevent the fastener from a movement in a direction that includes a component that is opposite to the direction of the clamping force, in particular in a direction that is opposite to the direction of the clamping force. In other words, the thermoplastic material (the securing element, as the case may be) can be arrangeable to prevent a loosening movement of the fastener relative to the implant part. This means, the fastener, the implant part and the thermoplastic material (the securing element, as the case may be) are equipped for the thermoplastic material (the securing element, as the case may be), after re-solidification, to secure the fastener against an axial (back-out) movement.

The fastener can include a thread. Then, the relative movement between fastener and implant part is generated by screwing in the fastener, for example in the bone, in an inner thread of the implant part, such as the tulip, or in an inner thread of another implant part, for example the second implant part. In such embodiments, the securing element can prevent the loosening movement, this means the axial (back-out) movement of the fastener either by preventing the axial (back-out) movement in general, for example by forming a stop and/or a by rotation lock as described below.

A blocking screw, for example used in femur treatment, a humeral nail, a traction bold, a clamp screw, for example used in a modular prosthesis, and a tensioning screw, for example used in a modular prosthesis, are example of fasteners including a thread.

The implant system can include at least one of these or comparable screws, and the securing element can be arrangeable to prevent the loosening movement of said screw(s).

In an embodiment, the fastener and the implant part are designed for allowing a variation of the angle of the fastener relative to the implant part or for preventing a variation of the angle of the fastener relative to the implant part. In both cases, the thermoplastic material (the securing element, as the case may be), the fastener and the implant part, can be designed for the thermoplastic material (the securing element, as the case may be), after re-solidification, to secure the fastener against an axial (back-out) movement. In the embodiment allowing for a variation of the angle of the fastener relative to the implant part, the thermoplastic material (the securing element, as the case may be), the fastener and the implant part, can be designed optionally for the thermoplastic material (the securing element, as the case may be), after re-solidification, to secure the fastener against said variation of the angle of the fastener relative to the implant part.

In particular, the thermoplastic material (the securing element, as the case may be) can be deformable to a first state and to a second state, wherein the thermoplastic material (the securing element, as the case may be) in the first state secures the fastener against axial (back-out) movement and wherein the thermoplastic material (the securing element, as the case may be) in the second state secures the fastener against axial (back-out) movement and against variation of the angle of the fastener relative to the implant part. Said securings can be established by the thermoplastic material in a direct or indirect manner. For example, the latter is the case if the thermoplastic material belongs to a securing element not consisting of the thermoplastic material, only.

Such an embodiment has the advantage that the surgeon can decide whether to allow for a variation of the angle of the fastener (e.g., screw) relative to the implant part (e.g., plate) or not together with securing the fastener (e.g., screw) against axial (back-out) movement.

Any embodiment including the thermoplastic material (the securing element, as the case may be), the fastener and the implant part designed for the variation of the angle of the fastener relative to the implant part and for the thermoplastic material (the securing element, as the case may be), after re-solidification, securing the fastener against said variation of the angle of the fastener relative to the implant part and against axial (back-out) movement has the advantage that the same fastener and hence the same fixation location can be used for both providing a fastener that can vary in angle with respect to the implant part and that can reliably fix the implant to the bone or to another implant part, for example.

In particular in embodiments in which the fastener is anchored in bone, for example by being a bone screw, this is a huge advantage over state-of-the art implant systems in which these two functions are spatially separated and hence need more bores in the bone and/or the plate.

For example, the fastener can be a screw, in particular a bone screw, and the implant part can be a fixation element, in particular a plate, such as a compression plate.

The fixation element of the implant system can be any fixation element used in osteosynthesis. In particular, the fixation element can be any plate used in osteosynthesis, in particular any plate used in a plate-screw-system.

For example, the plate can be a spinal, for example cervical, plate, a plate used in trauma surgery, a plate used in a joint prosthesis, such as a part of a hip socket (acetabulum) etc.

However, the thermoplastic material forms a positive-fit connection in a lateral wall of a through opening of the implant part (e.g. the plate) in many embodiments. Hence, the implant part can have a thickness of at least 1 mm, for example at least 1.5 mm or at least 2 mm.

For example, the lateral wall can include a cavity of at least 0.2 mm, for example of at least 0.5 mm measured along a longitudinal axis of the through opening of the implant part (e.g. plate) to form the positive-fit connection between the thermoplastic material and the implant part.

In an embodiment, the thermoplastic material is designed to form a cap at a proximal end of the fastener. Again, the thermoplastic material can be designed to form the cap in a direct or indirect manner.

In a variant of this embodiment, it is the securing element that is designed to form the cap.

The thermoplastic material or—as the case may be—the securing element can form the cap after re-solidification of the thermoplastic material, this means it can be equipped to be deformable into a cap.

However, the thermoplastic material (the securing element, as the case may be) can be designed to form the cap of the proximal end of the fastener prior and after liquefaction and re-solidification of the thermoplastic material. In such an embodiment, the thermoplastic material can be arranged to form, after re-solidification, the positive fit connection with another element of the implant system, for example the implant part.

Optionally, the thermoplastic material can be arranged to change, after re-solidification, the form of the cap. For example, the change of the form of the cap can cause the securing of the fastener against at least one of the axial (back-out) movement of the fastener, the rotation of the fastener relative to the implant part, and the variation of the angle of the fastener relative to the implant part.

In an embodiment, the thermoplastic material (the securing element, as the case may be) is designed to allow, after re-solidification of the thermoplastic material, access to the fastener, in particular to the proximal end of the fastener.

For example, the thermoplastic material (the securing element, as the case may be) is designed to form, after re-solidification of the thermoplastic material, a ring. The ring includes an opening arranged to allow access to the proximal end of the fastener.

In an embodiment, the thermoplastic material (the securing element, as the case may be) is removable. In other words, the fastener, the implant part and the thermoplastic material (the securing element, as the case may be) are equipped for the thermoplastic material, after re-solidification, to be removable.

For example, the thermoplastic material (the securing element, as the case may be) is designed to break under a predetermined mechanical load.

The specific mechanical load can be generated by a shear force generated by a rotation of the fastener. The rotation of the fastener can be caused by applying a torque to a proximal end of the fastener.

The rotation of the fastener can be a rotation of the fastener relative to the implant part. In particular, this can be the case if the thermoplastic material (the securing element, as the case may be) and the implant part are designed to form a positive-fit connection after re-solidification.

For example, the thermoplastic material (the securing element, as the case may be) can be designed to allow, after re-solidification of the thermoplastic material, access to the fastener, in particular to the proximal end of the fastener and the fastener can be equipped to engage with a screwdriver.

The specific mechanical load can be generated by a shear force generated by a relative axial movement between fastener and securing element. The relative axial movement can be generated by a relative rotation, for example if the fastener includes a thread.

The thermoplastic material (the securing element, as the case may be) can include a predetermined breaking point.

Removal of the securing element can be supported by softening the thermoplastic material, for example by a sonotrode equipped for both, applying ultrasonic vibrations and a torque (e.g., as described below).

In an embodiment, at least one of the fastener and the thermoplastic material (the securing element, as the case may be) is equipped to be guided by a tool, for example by the sonotrode.

In particular, the fastener can be equipped to engage with the tool in a manner that the angle between the fastener and the plate can be varied via the tool.

At least one of the fastener, the thermoplastic material (the securing element, as the case may be) and the implant part can include a guidance portion. The guidance portion can be an opening, for example a tool opening.

The guidance portion can be designed for preventing ultrasonic vibration, in particular ultrasonic vibration in an amount sufficient to liquefy the thermoplastic material, to be coupled into the thermoplastic material, for example by being designed to prevent ultrasonic vibrations to be coupled into the element of the implant system including the guidance portion.

For example, the guidance portion, the fastener, the implant part and the thermoplastic material can be designed for preventing ultrasonic vibration, in particular ultrasonic vibration in an amount sufficient to liquefy the thermoplastic material, to be coupled into the thermoplastic material.

Such a design of the guidance portion is important to guarantee that the thermoplastic material (the securing element, as the case may be) is decoupled vibrationally from the implant part and the at least one fastener.

The tool, for example an ultrasonic device, in particular the sonotrode, can include a guide portion, for example a distal protrusion. The guide portion can be equipped to guide the relative position between at least one of the sonotrode, the fastener, the thermoplastic material (the securing element, as the case may be) and the implant part.

The guide portion can be different from a portion of the sonotrode that couples the ultrasonic vibration for liquefaction of the thermoplastic material into the implant system.

The guide portion of the tool and the guidance portion of the fastener, the thermoplastic material (the securing element, as the case may be) and/or the implant part can complement each other in a manner that the tool is centred on at least one of a through opening for the fastener in the implant part, a bore in the bone and a thread, in particular an inner thread. The thread can be an inner thread of the fastener and/or an inner thread of another element of the implant system, for example the tulip of a screw.

In an embodiment, at least one of the implant system and the ultrasonic device, for example the sonotrode, can include means for preventing coupling of ultrasonic vibrations into the fastener and the implant part after the thermoplastic material (the securing element, as the case may be) has been brought in its final shape and position, at least.

For example, at least one of the implant system and the ultrasonic device, for example the sonotrode, can include a spacer, said spacer being arranged and/or designed in a manner that the coupling efficiency from the sonotrode into the implant system drops as soon as the thermoplastic material (the securing element, as the case may be) has been brought in its final shape and position. In other words, at least one of the implant system and the ultrasonic device can include a spacer, said spacer being equipped for preventing the coupling of ultrasonic vibration into the thermoplastic material after the thermoplastic material has been deformed into a predefined state. The predefined state can be the first or second state discussed above.

For example, at least one of the following can apply:
The spacer is of a material that does not transmit the ultrasonic vibrations.
The spacer has a contact surface to the implant system, in particular to the fastener and/or the implant part, that is disadvantageous for transmitting ultrasonic vibrations from the spacer to the implant system.
The spacer or the contact surface to the implant system is of a material that is disadvantageous for transmitting ultrasonic vibrations from the spacer to the implant system.
The spacer is in contact with the sonotrode or gets in contact with the sonotrode in a manner that it is not put in vibrations capable to liquefy the thermoplastic material. For example, the spacer can be a sleeve or sleeve-like element that is arranged or arrangeable around the sonotrode. The sleeve or sleeve-like element can be designed in a manner that it does not direct oscillations of the sonotrode to the implant system. For example, the sleeve or sleeve-like element is mounted on a component of the ultrasonic device, such as its housing, that does not vibrate in a manner contributing to the liquefaction of the thermoplastic material or the sleeve is connected to the sonotrode at one of the nodal points of the axially oscillating sonotrode.

In an embodiment, especially in an embodiment of the method, a control is provided that switches off the ultrasonic device, in particular the sonotrode, as soon as the thermoplastic material has been deformed into a predefined state.

The predefined state can be given by the ultrasonic device, for example the sonotrode, being in a final position relative to the implant system or by a set change in the coupling efficiency is measured. The former can include a measurement of the relative position between sonotrode and implant system, in particular fastener and/or implant part, the latter can includes a spacer as disclosed above.

The measurement of the relative position between ultrasonic device, for example the sonotrode, and implant system, in particular the fastener and/or implant part, can be done optically or acoustically, for example.

The control can include a spacer, for example the spacer described above.

According to a first aspect of the present invention, an implant system is provided, including an implant part, in particular a fixation element, such as a plate, for example a spinal plate, the system further including at least one fastener and the implant part having, for the fastener, for example for every fastener, a fastener receiving opening. The system also includes thermoplastic material (belonging to at least one element separate from the implant part and the fastener, belonging to the fastener, belonging to the implant part and/or possibly belonging to a sonotrode used for coupling energy into the system), the thermoplastic material being equipped for being liquefied by mechanical activation, especially ultrasonic vibration energy. The fastener and the implant part are equipped for the thermoplastic material, after re-solidification, to cause a connection, especially a positive-fit connection, between the fastener and the implant part, wherein the connection secures the fastener against at least one of an axial (back-out) movement of the fastener, a rotation of the fastener relative to the implant part, a variation of an angle of the fastener relative to the implant part. Especially, the thermoplastic material may fix the orientation of the fastener relative to the implant part with respect to all angular degrees of freedom, including a fixation against rotation around its own axis (fixation of the "roll" angle).

For example, an implant system according to the first aspect includes a plate, the plate being shaped to be placed against human or animal bone tissue, the system further including at least one fastener and the plate having, for the fastener, for example for every fastener, a fastener receiving opening, the system further including thermoplastic material, the thermoplastic material being equipped for being liquefied by mechanical activation, wherein the fastener and the plate are equipped for the thermoplastic material, after re-solidification, causing a connection between the fastener and the plate, wherein the connection secures the fastener against at least one of an axial (back-out) movement of the fastener, a rotation of the fastener relative to the plate, a variation of the angle of the fastener relative to the plate.

According to a second aspect of the present invention, an implant system is provided, including an implant part, in particular a fixation element, such as a plate, for example a spinal plate, the system further including at least one fastener and the implant part having, for the fastener, for example for every fastener, a fastener receiving opening. The system also includes thermoplastic material belonging to a securing element that is separate from the implant part and the fastener, that belongs to the fastener, that belongs to the implant part or that possibly belongs to a sonotrode used for coupling energy into the system. The thermoplastic material is equipped for being liquefied by mechanical activation, especially ultrasonic vibration energy. The fastener, the implant part and the securing element are equipped for the thermoplastic material, after re-solidification, to cause a connection, especially a positive-fit connection, with at least one of the fastener and the implant part, wherein the securing element secures the fastener against at least one of an axial (back-out) movement of the fastener, a rotation of the fastener relative to the implant part, a variation of an angle of the fastener relative to the implant part.

The securing element, in particular the thermoplastic material, can be equipped to cause a connection between the fastener and the implant part after re-solidification.

For example, an implant according to the second aspect includes a plate, the plate being shaped to be placed against human or animal bone tissue, the system further including at least one fastener and the plate having, for the fastener, for example for every fastener, a fastener receiving opening, the system further including a securing element including thermoplastic material, the thermoplastic material being equipped for being liquefied by mechanical activation, wherein the fastener, the plate and the securing element are equipped for the securing element, after re-solidification, securing the fastener against at least one of an axial (back-out) movement of the fastener, a rotation of the fastener relative to the plate, a variation of the angle of the fastener relative to the plate.

The securing element can consist of the thermoplastic material.

In both, the first and the second aspect, the mechanical activation is ultrasonic vibration that is decoupled vibrationally from the plate (implant part) and the at least one fastener, in preferred embodiments.

Various embodiments and features are disclosed in the following on the exemplary embodiment of the implant part being a plate, in particular a spinal plate, such as an anterior cervical plate. However, any embodiment and feature disclosed in the following can apply to any implant system and any aspect as described above. In particular any embodiment and feature disclosed in the following can apply to implant systems according to the first aspect (i.e. including thermoplastic material as described above) or to implant systems according to the second aspect (i.e. including the securing element as described above) if not otherwise stated.

In any embodiment, the implant system can include an energy director capable to define a spot at which liquefaction of the thermoplastic material sets in.

In particular, the energy director can be arranged on or formed by at least one of the fastener, the plate and the thermoplastic material. If the energy director is formed by the thermoplastic material, it can be given by a portion of the thermoplastic material that tapers towards a ridge or a tip.

In embodiments, the implant system includes a plurality of energy directors.

In a group of embodiments, the fastener receiving opening and the fastener are shaped so that the fastener can be inserted relative to the spinal plate at a variable angle.

In another group of embodiments, the fastener receiving opening and the shape of the fastener define the angle of the fastener relative to the plate. In these embodiments, the thermoplastic material does not need to fix the angle of the fastener axis relative to a plate plane; however, it may still fix the orientation of the fastener around its axis.

However, the fastener receiving opening and the shape of the fastener can be designed to allow for a change of the angle of the fastener relative to the plate plane after implantation of the plate and the fastener. In other words, the fastener receiving opening and the shape of the fastener, in particular the shape of a head portion of the fastener, can be designed in a manner that the fastener axis can change its orientation relative to a longitudinal axis of the fastener receiving opening and/or to the normal of a portion of a distal surface of the plate, said portion surrounding a distal opening of the fastener receiving opening.

The securing element or the thermoplastic material can be designed to prevent the change of the angle in embodiments in which the fastener receiving opening and the shape of the fastener are designed to allow for a change of the angle of the fastener relative to the plate plane after implantation of the plate and the fastener. In particular, the securing element or the thermoplastic material can prevent said change of the angle after re-solidification of the thermoplastic material.

Alternatively, the securing element or the thermoplastic material can be designed to allow for said change of the angle of the fastener relative to the plate plane or to allow for said change up to a maximal change in angle at least.

The securing element or the thermoplastic material can secure the fastener from the back-out movement in combination with a design that prevents the change of the angle or in combination with a design that allows for the change in angle up to a maximal change in angle at least.

In particular, the securing system or the thermoplastic material can form a rotation lock and/or a stop.

In implant systems according to the first aspect, the rotation lock and/or stop can be formed by a portion of the thermoplastic material that is not equipped to liquefy during an implantation method according to the invention. Further details concerning the implantation method are given below.

In implant systems according to the second aspect, the rotation lock and/or stop can be formed by a portion of the thermoplastic material that is not equipped to liquefy during an implantation method according to the invention or by a portion of the securing element that is not liquefiable, at least not liquefiable under the conditions during the implantation method.

The stop secures the fastener from the back-out movement in general.

The stop can be formed by liquefied and re-solidified thermoplastic material. In other words, the thermoplastic material can be designed to form the stop when liquefied by mechanical activation.

Alternatively, the thermoplastic material or the securing element can be pre-formed to include the stop.

The stop can be arranged or formed at a proximal end of the thermoplastic material or of the securing element.

The rotation lock is in particular advantageous in combination with a fastener that includes a thread. The rotation lock secures the fastener against a rotation of the fastener relative to the plate. This means, the rotation lock prevents the fastener from a rotation that causes a proximal movement of the fastener.

The rotation lock can be formed by liquefied and re-solidified thermoplastic material. In other words, the thermoplastic material can be designed to form the rotation lock when liquefied by mechanical activation.

In embodiments, the stop and/or rotation lock is arranged relative to the fastener to allow for the change of the angle of the fastener relative to the plate plane. For example, at least a portion of the stop and/or rotation lock can be separated by free space from the fastener and/or the stop and/or rotation lock can be elastically or plastically deformable in a manner that the stop still secures the fastener from the back-out movement after deformation and/or the rotation lock still secures the fastener against a rotation of the fastener relative to the plate.

A "distal" surface of the plate means a surface of the plate that is opposite to a surface of the plate that lays open to a user, for example a surgeon, during implantation of the system. The open laying surface is a proximal surface, then. Generally, the distal surface is a surface oriented towards the bone tissue to which the plate is to be secured.

In embodiments, the plate can be designed to bridge a gap between two bone portions, for example the gap between two vertebrae, the gap caused by a fraction or the gap caused by an osteotomy cut. The angle over which the fastener can change relative to the plate plane after implantation can be equal or smaller than an angle that is associated with a relative movement of the two bone portions during the healing procedure and/or during fusion.

In particular, the angle over which the fastener can change relative to the plate plane after implantation of the plate and the fastener can be equal or smaller than 25 degrees, in particular equal or smaller than 20 degrees, or equal or smaller than 15 degrees.

In embodiments, the plate is a spinal plate, the plate being shaped to be placed against at least one human vertebra. Hereinafter, the invention is described referring to the example of spinal plates, and all embodiments refer to spinal plates. However, the invention and its embodiments are not limited to spinal plates. Any characteristic or embodiment of a spinal plate described in this text may also apply to other systems in which a plate is secured to human or animal bone tissue, especially living bone tissue, even though it has been found out that the principles have special advantages if applied to spinal plates.

The thermoplastic material may be present as initially separate thermoplastic element, for example as initially separate securing element, or in the form of a plurality of initially separate elements, for example a plurality of initially separate securing elements. For example, the thermoplastic element(s) may be pin-shaped or have another generic shape. Alternatively, the thermoplastic element/elements may have a shape adapted to the shape of the fastener and/or the spinal plate.

The securing element can include a material that is not liquefiable or that is not able to liquefy during implantation. The securing element can distinguish from the thermoplastic element at least in this.

In addition or as an alternative, the spinal plate and/or the fastener may include the thermoplastic material or a fraction thereof, for example as a thermoplastic collar of the fastener or as a thermoplastic collar of the spinal plate. It is also possible that the spinal plate and/or even the fastener is made of thermoplastic material. In many embodiments, however, the fastener includes a body of a not liquefiable, for example metallic material, such as Titanium or steel. Especially, such body may form the enossal part including a thread (if any).

The following features may be present, alone or in any combination (the properties are described hereinafter with reference to one fastener; the considerations apply as options also for a plurality of fasteners):

The fastener has an outer thread for being anchored in the bone tissue. Especially, the fastener may have a shaft portion having the outer thread.

The fastener has a fastener head portion, and/or the fastener receiving opening is narrower on the distal side than on the proximal side.

The fastener and/or the fastener receiving opening has structures, for example undercut structures, for the thermoplastic material to flow into.

In embodiment, such structures may be provided in the form of an open porosity, for example of pores of 100-500 μm.

In embodiments, the structures are arranged at a location where they face the other one of the fastener/the fastener receiving opening, i.e. at an interface, whereby thermoplastic material after having flown is arranged between the fastener (for example fastener head) and the wall of the fastener receiving opening.

The fastener is free of any element that protrudes proximally above a proximal surface plane defined by the spinal plate.

The fastener has an insertion tool receiving structure with a non-circular cross section, for example for the purpose of screwing the implant into the bone tissue.

The insertion tool receiving structure may be an interior structure (such as a structure for receiving a key, for example a hexagon socket screw key or a torx key, etc.) and/or an exterior structure, such as a socket structure (hexagonal cross section for example).

If the fastener includes thermoplastic material, such insertion tool receiving structure may especially belong to a non-liquefiable part of the fastener (i.e. of material that does not liquefy at the temperature at which the thermoplastic material becomes flowable).

The insertion tool receiving structure may be accessible from the proximal side, i.e. it is initially not covered by thermoplastic material. It may become covered/filled with thermoplastic material during the process, as a consequence of making the thermoplastic material flowable.

The fastener may include a plurality of parts that are initially movable relative to each other and that during the process are fixable relative to each other.

Such parts may especially include an anchoring part that forms a shaft portion for being introduced into the bone tissue and for being anchored therein, for example the anchoring part having an outer thread, and an adjustment part.

In a group of embodiments, the adjustment part has an angle relative to the anchoring part that is variable/adjustable. In a sub-group of embodiments of this group, the angle may be fixed.

In a further group of embodiments, the angle between the axes of the anchoring part and the adjustment part is fixed/defined.

The fastener receiving opening and/or the fastener head may have a non-round outer shape, i.e. an outer shape ("outer" here refers to direction radial with respect to the proximodistal axis) that deviates from a circular symmetry, to contribute to a rotational fixation of the fastener relative to the spinal plate.

The fastener head has at least one through opening for a thermoplastic element to be inserted therethrough.

The plate has a distally extending collar around the fastener receiving opening that enhances the depth along which the fastener may engage.

The thermoplastic material is arranged/configured to, after re-solidification, at least partially cover the fastener from proximally and to be connected to the plate, to at least partially block the fastener against escaping towards proximally relative to the plate.

The system includes a backout prevention element that is configured to be connected to the plate and to block the fastener against escaping towards proximally relative to the plate. Such backout prevention element may include the thermoplastic material or portions thereof.

The plate may include structures, such as undercut structures, for thermoplastic material to lock the backout prevention element relative to the plate. Such structures may be in a proximally facing surface of the plate, near the fastener receiving opening, or may be inside the fastener receiving opening. A backout prevention element may be plate shaped, ring shaped, include a plurality of elements distributed around the periphery of the fastener receiving opening, or have any other shape.

The backout prevention element is an example of the securing element.

The backout prevention element is an example of the thermoplastic element.

For example, the system can include the backout prevention element including thermoplastic material as well as the fastener receiving opening and the fastener that are designed to allow for the change of the angle of the fastener relative to the plate plane after implantation. In this group of embodiments, the backout prevention element can include at least one of or the thermoplastic material of the backout prevention element can be arranged to form at least one of when being liquefied and re-solidified:
  a stop of any kind described above;
  a rotation lock of any kind described above.

Further, the backout prevention element can be designed to at least one of or the thermoplastic material of the backout prevention element can be arranged to at least one of when being liquefied and re-solidified:
  Restrict the change of the angle between the plate plane and the fastener after implantation to a maximal angle, for example to a maximal change of 25, 20 or 15 degrees;
  Allowing for the variation of the angle of the fastener by a movement of the fastener in a first direction and secures the fastener against the variation of the angle of the fastener by a movement of the fastener in a second direction. In other words, the backout prevention element prevents the fastener from changing its angle relative to the plate plane by a movement in the first direction but not by a movement in the second direction. Such a prevention of a variation of the angle by a movement of the fastener axis in a plane can be established by a local deformation of the thermoplastic element or by using thermoplastic elements that are restricted in their extension.
  Prevent the fastener from changing its angle relative to the plate plane.

However, the backout prevention element can also be designed to have no influence on the change of the angle between the plate plane and the fastener after implantation.

In embodiments of the system in which the backout prevention element allows for a change of the angle between the plate plane and the fastener after implantation, the system can include after implantation at least one of:
  A backout prevention element that is deformable to allow the change of angle of the fastener relative to the plate plane;
  Free space between the implant and a portion of the backout prevention element that is arrange to prevent the implant from backout.

In embodiments, at least one of the following can apply:
  The implant system including an implant part, the system further including at least one fastener and the implant part having, for the fastener, for example for every fastener, a fastener receiving opening, the system further including a securing element including thermoplastic material, the thermoplastic material being equipped for being liquefied by mechanical activation, wherein the fastener and the implant part and the securing element are equipped for the securing element, after re-solidification, to secure the fastener against at least one of an axial (back-out) movement of the fastener, a rotation of the fastener relative to the implant part, a variation of the angle of the fastener relative to the implant part.

In addition, the fastener receiving opening and the shape of the fastener can be designed to allow for a variation of the angle of the fastener relative to the implant part, and wherein the securing element is equipped for allowing a variation of the angle of the fastener relative to the implant part and for securing the fastener against the axial (back-out) movement after re-solidification at least.

The implant part can be a plate, the plate being shaped to be placed against human or animal bone tissue.

The mechanical activation is ultrasonic vibration. In many embodiments, the thermoplastic material is decoupled vibrationally from the implant part and the at least one fastener.

In addition, at least one of the following can apply:
  The securing element forms at least one of a stop and a rotation lock or wherein the securing element is equipped for deforming in a manner that it forms at least one of a stop and a rotation lock, wherein it is the thermoplastic material of the securing element that forms at least one of the stop and the rotation lock or wherein the thermoplastic material of the securing element is equipped for deforming in a manner that it forms at least one of the stop and the rotation lock.
  The securing element is equipped for allowing the variation of the angle of the fastener relative to the implant part by being deformable, wherein it is the thermoplastic material of the securing element that is equipped for allowing the variation of the angle of the fastener relative to the implant part by being deformable.
  The securing element is equipped to define a maximal angle up to which the fastener can vary relative to the implant part.

The implant system can be a spinal implant system including an implant part that is a plate.

In particular, the implant system can be according to any embodiment and can be a spinal implant system, wherein the plate is a spinal plate, in particular an anterior cervical plate.

In particular, the fastener receiving opening and the fastener can be shaped so that the fastener can be inserted relative to the spinal plate at a variable angle.

The implant system can be according to any embodiment, wherein the fastener is elongate with a longitudinal axis extending proximodistally.

The implant system according to any embodiment, wherein the thermoplastic material belongs to at least one thermoplastic element that is separate from the fastener and separate from the implant part, in particular from the implant part being the plate.

The implant system according to any embodiment, wherein at least one of the fastener and of the implant part, in particular of the implant part being the plate, includes the thermoplastic material.

The implant system according to any embodiment, wherein the fastener has an outer thread for being anchored in the bone tissue.

The implant system according to any embodiment, wherein the fastener has a fastener head portion, and/or the fastener receiving opening is narrower on the distal side than on the proximal side.

The implant system according to any embodiment, wherein the fastener is free of any element that protrudes proximally above a proximal surface plane defined by the implant part, in particular by the implant part being the plate.

The implant system according to any embodiment, being equipped for the thermoplastic material to be, after re-solidification, connected to the implant part, in particular to the implant part being the plate, and to at least partially block the fastener against escaping towards proximally relative to the implant part (the plate).

The implant system according to any embodiment including a backout prevention element having the thermoplastic material or at least a portion thereof.

For example, the backout prevention element is at least one of plate shaped or ring shaped or includes a plurality of elements distributed around the periphery of the fastener receiving opening.

The implant system according to any embodiment, wherein the thermoplastic material belongs to at least one of: a separate element, the plate, the fastener, a sonotrode.

In embodiments in which the fastener includes a structure that is designed to direct liquefied thermoplastic material in a predefined direction, the thermoplastic material can be further designed to form an anchorage in the implant part, in particular in the implant part being the plate.

Alternatively or in addition, in embodiments in which the fastener includes a structure that is designed to direct liquefied thermoplastic material in a predefined direction, the implant part, in particular the implant part being the plate, includes the structures for the thermoplastic material to flow into and wherein the predefined direction is a direction to a first region of the structure that is designed to direct liquefied thermoplastic material, wherein a condition for thermoplastic material to flow into the structure for the thermoplastic material to flow into is fulfilled at the first region, wherein the condition is not fulfilled at a region different from the first region of the structure that is designed to direct liquefied thermoplastic material.

For example, the fastener receiving opening and the fastener are shaped so that the fastener can be inserted relative to the spinal plate at a variable angle and wherein said condition is fulfilled for any angle at least at a region of the structure that is designed to direct liquefied thermoplastic material.

In embodiments in which the implant part, in particular the implant part being the plate, includes the thermoplastic material and wherein the thermoplastic material is arranged to form a proximal portion of the fastener receiving, the thermoplastic material can extend beyond a proximal surface of the implant part, said surface not including the thermoplastic material.

Alternatively or in addition, the fastener can include a fastener head with a recess arranged to accommodate liquefied thermoplastic material.

In accordance with an option, the fastener may be an implant as disclosed in WO 2011/054124, especially as defined in any one of claims 1-12 thereof and as shown in the figures, namely an anchor device that has a longitudinal bore extending distally from a proximal end, and at least one hole from the longitudinal bore outward, wherein liquefiable thermoplastic material may be pressed through the longitudinal bore and through the hole into cancellous bone tissue to have, after re-solidification, an anchoring effect.

The energy to be applied to the thermoplastic material for making it flowable may be mechanical energy, especially mechanical vibration energy. For applying the energy, a vibrating tool (sonotrode) press the thermoplastic material into the gap.

Other forms of energy, such as radiation energy, inductive heat, etc. are not excluded.

The invention also concerns a method of implanting a system of the above-described kind in any embodiment.

In an embodiment, the method is a method of implanting a spinal plate, especially according to any embodiment, in a human or animal vertebra, the method including the steps of placing the spinal plate relative to the bone tissue and anchoring the fastener implant in the bone tissue, causing energy to impinge on thermoplastic material until a flow portion thereof becomes flowable and flows relative to the spinal plate and the fastener, stopping the energy transfer, and causing the thermoplastic material to re-solidify, whereby an angular orientation of the fastener relative to the spinal plate is fixed by the thermoplastic material.

Preferably, the energy is mechanical vibration energy. In particular, the energy is ultrasonic vibration energy.

In an embodiment, the method is a method of implanting a spinal plate, especially according to any embodiment, in a human or animal vertebra, the method including the steps of placing the spinal plate relative to the bone tissue and anchoring the fastener in the bone tissue, causing energy to impinge on the securing element including thermoplastic material until a flow portion of the thermoplastic material becomes flowable and flows relative to the spinal plate and the fastener, stopping the energy transfer, and causing the thermoplastic material to re-solidify, whereby a backout prevention element is formed.

The fastener, the plate and the securing element (the backout prevention element) can be formed to allow for a variation of the angle of the fastener relative to the plate after implantation.

Mechanical vibration or oscillation suitable for devices according to embodiments of the invention and according methods that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (sonotrode) is e.g. designed such that its contact face oscillates predominantly in the direction of the element axis (longitudinal vibration) and with an amplitude of between 1 and 100 µm, preferably around 20 to 90 µm. Rotational or radial oscillation is possible also.

The preferred amplitude depends on various parameters, such as the thermoplastic material and the shape of the thermoplastic material. For example, the following has been found experimentally for ring-like and cap-like thermoplastic material, wherein cap-like thermoplastic material distinguishes from ring-like thermoplastic material by including a distal protrusion. An exemplary embodiment of ring-like thermoplastic material is shown in FIGS. 46 and 48 and exemplary embodiments of cap-like thermoplastic material are shown in FIGS. 51-54, for example:

An amplitude of 20-40 μm can be favorable for amorphous, e.g., resorbable polymers like PLAs, PGAs, PLGAs etc., and a thermoplastic element in the shape of a ring having a diameter of around 4-5 mm.

An amplitude of 60-90 μm can be favorable for semicrystalline, high melting point polymers, such as PEEK or PA. For example, amplitudes at the lower limit of the range can be favorable for PA elements in the shape of a cap having a diameter of around 4-5 mm, whereas amplitudes at the upper limit of the range can be favorable for PA elements in the shape of a ring having a diameter of around 4-5 mm and for PEEK elements in the shape of a cap having a diameter of around 4-5 mm.

In particular, the amplitudes are preferred, i.e. optimized, in terms of short times for local liquefaction, minimal or no heating of tissue and other parts of the implant system, and minimal mechanical load on the thermoplastic material and hence on the tissue. In particular, the time for local liquefaction can be below 5 s, for example below 2 s, such as between 1 and 2 s.

For specific embodiments of devices, it is possible also to use, instead of mechanical vibration, a rotational movement for creating the named friction heat needed for the liquefaction of the anchoring material. Such rotational movement has preferably a speed in the range of 10'000 to 100'000 rpm.

A further way for producing the thermal energy for the desired liquefaction includes coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infrared frequency range is used, wherein the preferred radiation source is a corresponding laser. Electric heating of one of the device parts may also be possible.

In this text the expression "thermoplastic material being liquefiable, e.g., by mechanical vibration" or in short "liquefiable thermoplastic material" or "liquefiable material" is used for describing a material including at least one thermoplastic component, which material becomes liquid (flowable) when heated, in particular when heated through friction, i.e., when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 μm and 100 μm, preferably around 20-90 or 20-70 μm. Such vibrations are e.g. produced by ultrasonic devices as, e.g., known for dental applications.

In this text, generally a "non-liquefiable" material is a material that does not liquefy at temperatures reached during the process, thus especially at temperatures at which the thermoplastic material of the fastener is liquefied. This does not exclude the possibility that the non-liquefiable material would be capable of liquefying at temperatures that are not reached during the process, generally far (for example by at least 80° C.) above a liquefaction temperature of the thermoplastic material or thermoplastic materials liquefied during the process. The liquefaction temperature is the melting temperature for crystalline polymers. For amorphous thermoplastics the liquefaction temperature is a temperature above the glass transition temperature at which the becomes sufficiently flowable, sometimes referred to as the 'flow temperature' (sometimes defined as the lowest temperature at which extrusion is possible), for example the temperature at which the viscosity drops to below $10^4$ Pa*s (in embodiments, especially with polymers substantially without fiber reinforcement, to below $10^3$ Pa*s)), of the thermoplastic material.

For example, a non-liquefiable material may be a metal, or ceramic, or a hard plastic, for example a reinforced or not reinforced thermosetting polymer or a reinforced or not reinforced thermoplastic with liquefaction temperature considerably higher than the liquefaction temperature of the liquefiable material, for example with a melting temperature and/or glass transition temperature higher by at least 50° C. or 80° C. or 100° C.

There is a variety of thermoplastic materials commercially available—as shown below. The thermoplastic material used in embodiments of the invention can depend on the purpose of a specific embodiment:

A thermoplastic material having an elasticity coefficient of more than 1 GPa is preferably chosen if the thermoplastic material (the securing element, as the case may be) is equipped for securing the fastener against a variation of the angle of the fastener relative to the implant part, at least. A thermoplastic material having an elasticity coefficient of more than 1 GPa is also called a hard thermoplastic material in the following.

In addition or alternatively, hard thermoplastic materials can be used for at least one of securing the fastener against an axial (back-out) movement and against a rotation of the fastener relative to the implant part.

For example, hard thermoplastic material can be used to prevent axial (back-out) movement only. In this case, angulation (i.e., variation of the angle of the fastener relative to the implant part) can be enabled by adapting at least one of the design of the thermoplastic material (the thermoplastic element, the securing element) and form fitting geometries of the fastener and the implant part. For example, at least one of the following can apply:

Space for angulation can be provided, for example as shown in FIGS. 39-40, 42-44, 46-48.

In particular, space for angulation is provided in combination with geometries of the fastener and the implant part, in particular of the fastener head and the fastener receiving opening, that allow for angulation.

By positioning the securing function close to a center of rotation or close to the centers of rotation. By this, material strain caused by angulation can be kept below 5%, or below 1%, for example.

Such an arrangement of the securing function is advantageous for keeping the deformation of the thermoplastic material below a critical deformation limit, for example a critical deformation limit with respect to alternating strain.

A center of rotation can be a point on an axis around which the fastener rotates when it varies the angle relative to the implant part, for example.

A fastener that can angulate in a plurality of direction can have a plurality of centers of rotation.

A positioning of the securing function close to the center of rotation is provided in combination with geometries of the fastener and the implant part, in particular of the fastener head and the fastener receiving opening, that allow for angulation.

A variation of the angle in a specific plane at least can remain unlocked, for example by a design of the thermoplastic material (the thermoplastic element, the securing element) and of its fixation to the implant part that allows for a variation in angle in a specific plane at least. Related exemplary embodiments are discussed with respect to FIG. 19, for example.

A variation of the angle that remains unlocked in a specific plane at least is provided in combination with geometries of the fastener and the implant part, in particular of the fastener head and the fastener receiving opening, that allow for angulation.

It is an advantage of a thermoplastic material having a high elasticity coefficient of more than 1 GPa that the thermoplastic material allows minimal movements and displacements, only. This is an important characteristic if the fastener is a tensioning element, such as a tensioning screw (turnbuckle, clamp screw), for example.

However, the minimal movements and displacements can be important as they allow for relative movement of two bone portions during healing and/or fusion and as they reduce the deformation of the implant part due to such relative movements, for example. The latter reduces the risk of a failure of the implant part, for example due to critical plastic deformation.

The thermoplastic material can be a hard thermoplastic material by including fillers, for example fibers. In other words, the hard thermoplastic material can be a fiber reinforced thermoplastic material.

For example, the hard thermoplastic material can include 10-60% by weight, for example 20-40% by weight of carbon fibers.

PEEKs, PAs, and fiber reinforced thermoplastic materials are examples of hard thermoplastic materials that can be used in embodiments of the implant system. In particular, Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, and Polyoxymethylene are examples of preferred hard thermoplastic materials.

Hard materials, in particular PEEK, are suitable materials for securing the fastener against axial (back-out), against variation of the angle relative to the implant part, or against rotation relative to the implant part as well as against any combination of said movements.

A thermoplastic material having an elasticity coefficient between 0.05 and 1 GPa, for example between 0.5 and 1 GPa, can be chosen if the thermoplastic material (the securing element, as the case may be) is equipped for securing the fastener against an axial (back-out) movement of the fastener, in the first instance.

A thermoplastic material having an elasticity coefficient between 0.05 and 1 GPa, for example between 0.5 and 1 GPa, is also called a soft thermoplastic material in the following.

A soft thermoplastic material has the advantage that is allows some movements and displacements. This is important in embodiments including a thermoplastic material (a securing element, as the case may be) equipped for securing the fastener against axial (back-out) movement but allowing for a variation of the angle of the fastener relative to the implant part.

Polycarbonateurethane (in particular Bionate® by DSM, especially Bionate 75D and Bionate 65D) is/are examples of preferred soft thermoplastic materials.

An elasticity coefficient of at least 0.5 GPa also ensures that the liquefiable material is capable of transmitting the ultrasonic oscillation with such little damping that inner liquefaction and thus destabilization of the liquefiable element does not occur, i.e., liquefaction occurs only where the liquefiable material is at a liquefaction interface to a stop face. The plastification temperature of the thermoplastic material used in embodiments of the invention is preferably of up to 200° C., between 200° C. and 300° C. or even more than 300° C.

As pointed out above, PEEK can be a good choice for many embodiments. In this case, the plastification temperature is between 350° C. and 400° C.

Depending on the application, the liquefiable thermoplastic material may or may not be resorbable. In many embodiments, there is no need for a resorbable thermoplastic material. However, embodiments in which the fastener, the implant part and the thermoplastic material (the securing element, as the case may be) are equipped for providing further properties besides securing the fastener against at least one of an axial (back-out) movement of the fastener, a rotation of the fastener relative to the implant part, a variation of the angle of the fastener relative to the implant part, can include a resorbable thermoplastic material.

For example, the further properties can be:

Removability of the fastener.

Preventing thermoplastic material, for example fragments thereof or of the securing element, from remaining permanently in the body. Such fragments can be created during removal of the fastener, for example.

Continuous reduction of the connection between fastener and implant part. Thereby, the healed bone or fused bone portions take over load bearing after an initial healing/fusion phase.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials.

Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Bohringer Ingelheim, or a polyether etherketone such as PEEK 450G from Invibio, UK.

The above list of non-resorbable polymers includes polymers with an elasticity coefficient that is below 0.5 GPa, for example polyolefins and polyurethane (which is a thermoplastic elastomere). Thermoplastic materials of this kind can also be used in some specific embodiments of the invention—in particular in embodiments aiming for securing the fastener against axial (back-out) movement and allowing the fastener for an extensive variation of the angle of the fastener relative to the implant part. In particular, the locking of the fastener can be elastic. This means that the locking is also less sensitive to micro movements and/or alternating load. FIG. 41 shows a possible exemplary embodiment of a thermoplastic element that can be elastically deformable.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www-.matweb.com by Automation Creations, Inc.). An overview table of polymers and applications is listed in Wintermantel, page 150; specific examples can be found in Wintermantel page 161 ff. (PE, Hostalen Gur 812, Hochst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The liquefiable material having thermoplastic properties may contain foreign phases or compounds serving further functions. In particular, the hard thermoplastic material may be strengthened by admixed fillers, for example fibers, e.g. carbon fibers that may increase strength and wear resistance.

If the liquefiable material is to be liquefied not with the aid of vibrational energy but with the aid of electromagnetic radiation, it may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

The fastener and/or implant part, for example the (spinal) plate may (with the possible exception of the thermoplastic material, if the thermoplastic material belongs to the fastener/the spinal plate) be of a metal, for example a titanium alloy. A preferred material is titanium grade5. Alternative materials are other metals like other titanium alloys, stainless steel, or hard plastics such as PEEK etc.

BRIEF DESCRIPTION OF THE DRAWINGS

In the following, ways to carry out the invention and embodiments are described referring to drawings. The drawings mostly are schematical. In the drawings, same reference numerals refer to same or analogous elements. The drawings show:

FIGS. 2-5, 7-17, 20, 21, 23, 24, 27-29, 32-35, 38-40, 42-49 and 51-54 sections through spinal plates and/or fasteners or portions thereof.

DESCRIPTION OF THE PREFERRED EMBODIMENTS

Figure 1:
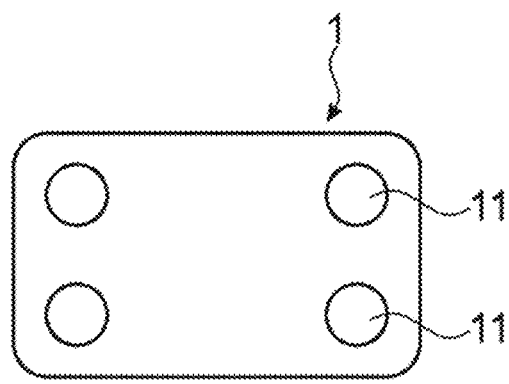
FIGS. 1, 6, 18, 19, 26, 30, 31, 36, 37 and 41 top views of a spinal plate, or a part thereof, in FIGS. 6, 19, 36, 37 and 41 with an inserted fastener screw.

FIG. 1 shows a spinal plate 1. The plate may have a shape adapted to the human spine. It has a plurality of fastener receiving locations, for example being constituted by appropriately shaped through openings 11. The fastener receiving locations are equipped for receiving fasteners by which the spinal plate is fastened to the vertebra.

Figure 2:
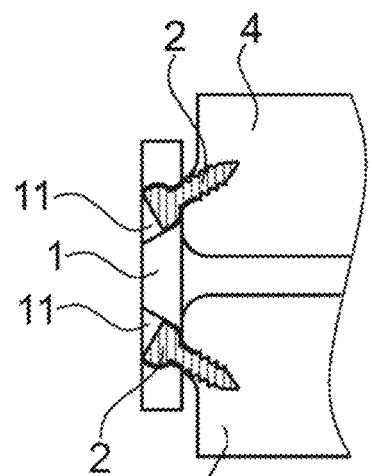

FIG. 2 very schematically shows such a spinal plate attached to a vertebra for stabilizing it. In the depicted configuration, the spinal plate, being shown in section through two fastener receiving openings 11, is attached to the anterior side of two neighboring vertebral bodies by fasteners 2, here very schematically illustrated to be surgical screws. The spinal plate of FIG. 1 is thus an anterior plate, for example an anterior cervical plate (ACP). The spinal plate of FIG. 1 has four fastener receiving locations, two for each vertebral body.

However, the current invention also applies to:
spinal plates configured to be attached to other parts of the spine than the cervical spine, for example the thoracic spine or the lumbar spine.
spinal plates configured to be attached to other locations than the anterior side of the spine, for example the lateral side or the posterior side
spinal plates configured to be attached not only to two neighboring vertebra but to for example more than two vertebra and/or to vertebra that are not immediate neighbors of each other
spinal plate systems with other fasteners than surgical screws, for example fasteners that are anchored by thermoplastic material that during implantation is liquefied and thereafter re-solidifies to yield a positive fit connection with the bone tissue, as for example described in WO 02/069 817, WO 2004/017 857, WO 2010/096942, or WO 2011/054124.

Figure 3:
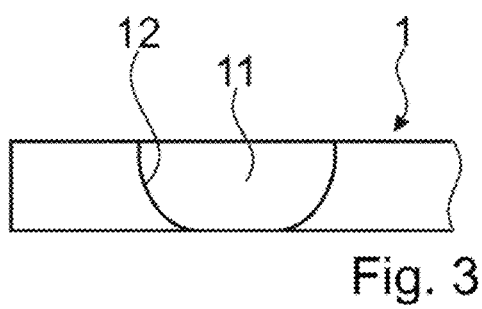

FIG. 3 schematically illustrates a partial cross section through a spinal plate 1 and more particularly through a fastener receiving opening 11 thereof. The opening is broader proximally than distally and has a lateral side wall 12 that in the depicted configuration is slightly concavely curved.

Figure 4:
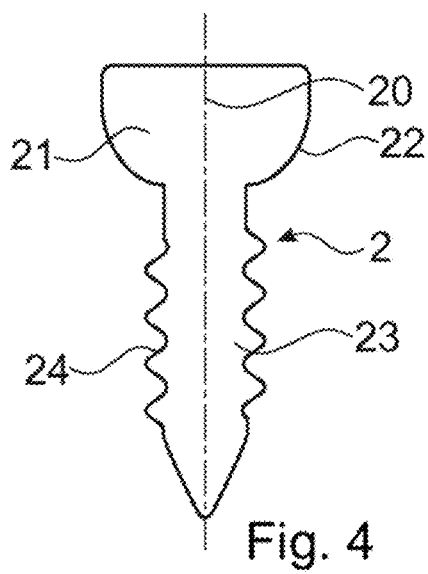

FIG. 4 shows an example of a fastener 2 being a surgical screw. The screw has a screw head 21 with an outer surface 22, for example, adapted to the lateral side wall 12 so that the direction of the screw axis 20 relative to the spinal plate 1 is adjustable at least to some extent, i.e., the fastener may secure the plate to the bone tissue at different angles that may depend on the clinical situation. The fastener (here: screw) in addition to the fastener head further has a fastener shaft 23 that may—if the fastener is a screw—include an outer thread 24. If the fastener is a fastener that uses thermoplastic material for anchoring, the fastener shaft may in addition or as an alternative include other structures, for example openings through which the thermoplastic material may be pressed into the tissue, and/or surface portions of thermoplastic material.

Figure 5:
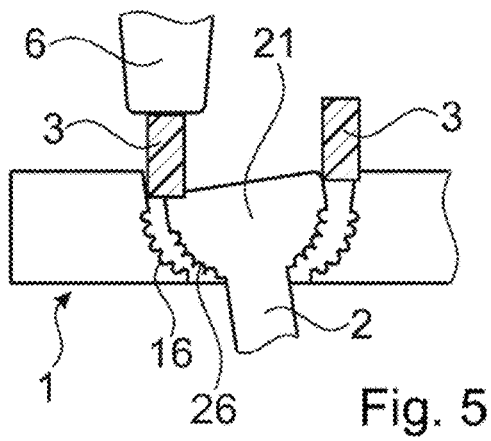

FIG. 5 shows an example of a fixation principle for fixing a fastener 2, after implantation thereof, to the spinal plate 1 by thermoplastic material. At least one thermoplastic element 3 in a solid state is brought into contact with the plate 1 and or the fastener 2 in a vicinity of the fastener receiving location, and a sonotrode 6 is used to impinge the thermoplastic element 3 with mechanical vibration energy until thermoplastic material of the thermoplastic element 3 becomes flowable and flows relative to the spinal plate 1 and the fastener 2, in particular the fastener head 21, whereby, after re-solidification, it secures the spinal plate 1 and the fastener 2 relative to each other by being in physical contact with both. This fixation may be provided with additional stability if the spinal plate along the lateral side wall and/or the fastener head is provided with additional structures 16; 26, for example substantial surface roughness and/or undercut structures, such as a region of an open porous structure, capable of making a positive fit connection with liquefied material that has interpenetrated them.

Figure 6:
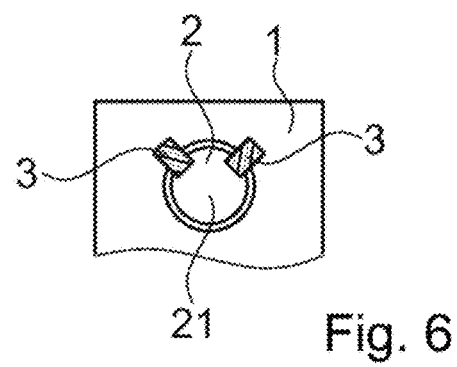

FIG. 6 showing a schematical top view of a spinal plate 1 with a single fastener 2, illustrates the principle that, especially for an embodiment of the principle shown in FIG. 5, the thermoplastic material need not be distributed around the full periphery of the fastener head 21 (although such distribution around the periphery is an option) but may be confined to at least one discrete location, with at least one thermoplastic element 3 being provided for each location.

Figure 7:
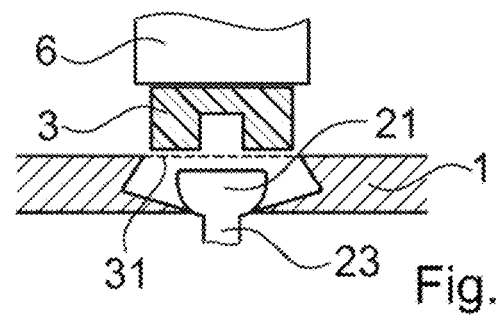

FIG. 7 shows an embodiment in which in contrast to the embodiment of FIG. 5 there is not only a small gap between the fastener head 21 and the lateral wall of the fastener receiving opening but in which fixation includes molding the fastener head 21 into a hollow space defined by the fastener receiving opening. To this end, for example, a comparably large thermoplastic element 3 or a plurality of thermoplastic elements with an accordingly large cumulated volume may be used. In this embodiment, especially the proximal end of the fastener head may be cast into the thermoplastic material. In FIG. 7, a possible level of the thermoplastic material after re-solidification is illustrated by a dashed line 31.

FIG. 8 illustrates the principle that in embodiments like the one of FIG. 7, depending on the orientation of the fastener, the thermoplastic material may be subject to an anisotropic flow during the process (arrow 31). FIG. 8 also illustrates a possible excess projection (by Δh) after the process, which excess projection depending on the clinical situation should be minimal only, and may be evenly distributed.

FIG. 9 shows an embodiment based on a similar principle as the embodiment of FIGS. 7 and 8. However, in contrast to these, the fastener 2 has an undercut portion 27 into which flowable thermoplastic material penetrates to yield, after re-solidification, a positive fit connection. This may optionally be combined with structures 16 of the kind shown in FIG. 5.

FIG. 10 illustrates the principle (that is applicable to all embodiments described hereinbefore and unless stated otherwise to all embodiments described hereinafter) that the thermoplastic material or at least a portion thereof may, instead of being provided as separate element, initially belong to the fastener. To this end, the fastener head 21 is at least partially made of a thermoplastic portion 41. When the vibration energy impinges, the thermoplastic portion 41 at least partially becomes flowable and flows relative to any non-liquefiable portion of the fastener (and/or relative to portions of the thermoplastic material that are not to flow) and relative to the spinal plate 1 for fixing the fastener relative to the spinal plate substantially as described hereinbefore.

In the embodiment of FIG. 10, the thermoplastic portion 41 has a longitudinal through opening 42 for a tool engaging into a tool opening 28 (an example of an insertion tool receiving structure), of the non-liquefiable portion of the fastener, with a non-circular cross section for the purpose of screwing the implant into the bone tissue.

FIG. 10 also illustrates an optional separate thermoplastic element 3 that may be welded to the thermoplastic portion 41 of the fastener in addition to the thermoplastic portion 41 being made flowable and caused to flow relative to the spinal plate 1 or instead of this.

FIG. 11 shows an example in which the fastener 2 has an anchoring part 25 (base part) forming the shaft and has an adjustment part 51 that is mounted relative to the anchoring part with an angle being adjustable prior to the implantation and during the implantation. In the depicted embodiment, the adjustment part 51 has a ball portion 52 engaging in a corresponding indentation 29 of the anchoring part and has a pin portion 53, possibly with undercut structures (not shown) protruding proximally. The angle between the anchoring part and the adjustment part may be fixable by conventional means, such as jamming, if necessary. The thermoplastic fixation element 3 fixes the adjustment part with the anchoring part attached to the plate 1 for example in the manner described hereinbefore.

In the embodiment of FIG. 12, the anchoring part 25 of the fastener has a ball portion 71 with an open porous region 72. The adjustment part 51 has, towards distally, a corresponding shape, whereby it can be clipped onto the ball portion 71. For fixing the adjustment part relative to the anchoring part and for fixing the fastener relative to the spinal plate 1, the thermoplastic fixation element 3 is brought into contact with both, the adjustment part and the porous region 72 while mechanical vibration energy impinges, whereby thermoplastic material is made flowable and in addition to flowing relative to the spinal plate and the adjustment part to fix, after re-solidification, the fastener relative to the spinal plate, the thermoplastic material also flows into the open porous region 72 of the anchoring part, whereby it fixes the relative orientation.

FIG. 12 also illustrates an optional stepped bore in the bone tissue 100 to accommodate the adjustment part.

The embodiment of FIG. 12 also works if the adjustment part is one-piece with the spinal plate.

FIG. 13 shows an embodiment in which the spinal plate 1 has a thermoplastic portion 85 accessible from the distal side. The fastener 2 has a fixation structure 81 that may include an undercut. In this embodiment, the mechanical vibration energy directly impinges on the spinal plate while the thermoplastic portion 85 is in contact with the fixation structure until thermoplastic material becomes flowable and flows relative to the fixation structure, whereby after re-solidification thermoplastic material of the thermoplastic portion 85 embeds the fixation structure and thereby fixes the fastener relative to the spinal plate in a defined orientation.

Figure 14:
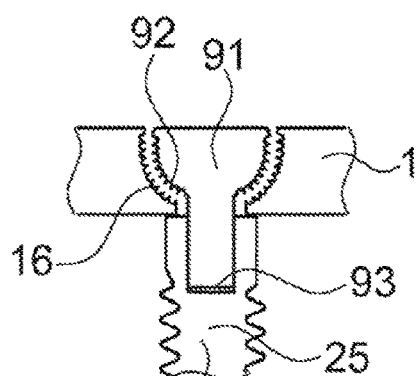

FIG. 14 shows a further embodiment with a two-part fastener, namely an anchoring part 25 and a fixation part 91. In contrast to the adjustment part of embodiments described hereinbefore, the fixation part has a fixed angle relative to the anchoring part 25 and is always co-axial with the latter. The fastener includes thermoplastic material 93 at an interface between the anchoring part and the fixation part (i.e. at least one of the anchoring part and of the fixation part includes thermoplastic material), whereby the fixation part is capable of being mounted to the anchoring part by being pressed against the anchoring part while mechanical vibration energy impinges on it. There is also thermoplastic material 92 at an interface between the fixation part and the spinal plate 1 (for example near structures 16 as described hereinbefore).

The embodiment of FIG. 14 can be applied as follows: in a first step, the anchoring part is implanted in the bone tissue, in an orientation chosen depending on the clinical situation. Then, the spinal plate and the fixation part are placed relative to the bone tissue and the anchoring part. Thereafter, a sonotrode is used to press the fixation part towards distally and to couple vibration energy into the fixation part until the thermoplastic material 92, 93 becomes flowable and flows to fix, after re-solidification, the fixation part both, to the anchored anchoring part and to the spinal plate 1, in the orientation defined by the anchoring part.

The two-part structure of the fastener in this embodiment is not used for defining and fixing the orientation of the parts relative to one another but to make the described two-step implantation procedure possible, wherein the second step includes a movement relative to the anchored anchoring part and includes fixing the fastener relative to the spinal plate.

Figure 15:
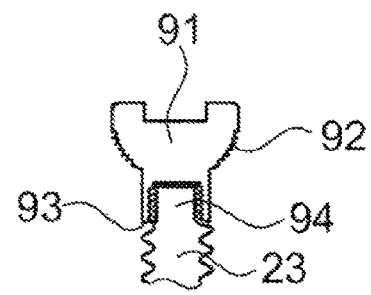

The embodiment of FIG. 15 is based on the same principle, but in contrast to the embodiment of FIG. 14, the anchoring part has a pin portion (or post) 94 and the fixation part has a corresponding indentation, and not the other way round as in FIG. 14.

Figure 16:
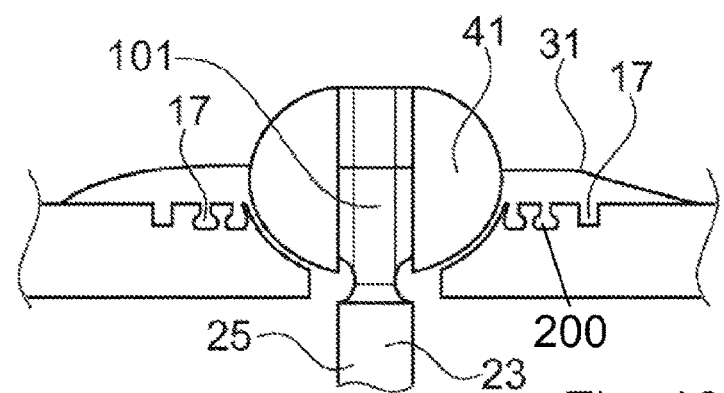

The embodiment of FIG. 16 has, similarly to the embodiment of FIG. 10, a fastener with a thermoplastic portion 41. In contrast to FIG. 10, the spinal plate 1 has securing structures 17 on the proximally facing surface thereof, and thermoplastic material of the thermoplastic portion is, after the process, distributed over the proximally facing surface to flow into these structures to fix the fastener in the actual orientation relative to the spinal plate (see surface 31 after the process). The securing structures 17, like the previously described structures 16 along the wall of the fastener receiving openings—may include undercut structures 200.

In the embodiment of FIG. 16, the anchoring part has a head 101 with a non-round (for example, hexagonal) cross section onto which the thermoplastic portion 41 is cast; this being a feature independent of the other features of this configuration.

Figure 17:
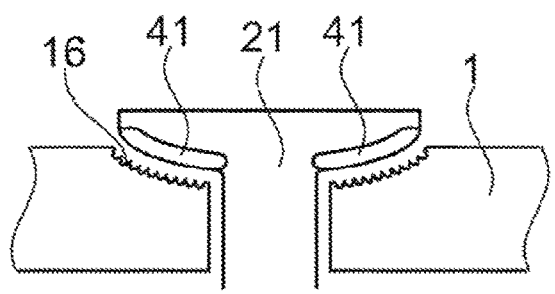

FIG. 17 illustrates a variant in which the spinal plate at the position of the fixation structures 16 is indented, whereby the part with the fixation structures may be viewed as a broadening of the fastener receiving opening. The thermoplastic portion 41 is present as a cushion on the distal side of the head portion 21 of the fastener.

In embodiments like the ones of FIGS. 16 and 17, the structures 16; 17 need not be evenly distributed around the periphery of the fastener receiving opening but may be in a not circularly symmetrical configuration. An example of such configuration is sketched in FIG. 18. Such not circularly symmetrical configuration provides additional stability against rotation, especially if indentations (as illustrated in FIG. 17 or also in FIG. 20 described hereinafter, for example) have such a not circularly symmetrical configuration.

Figure 19:
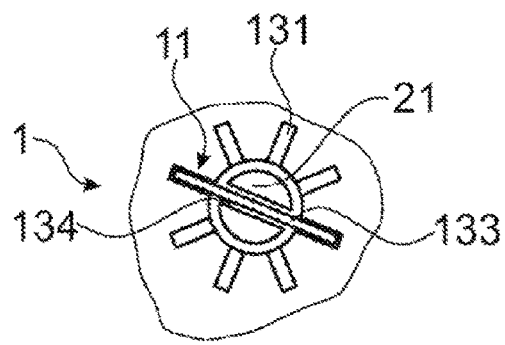

FIG. 19 shows an other measure for fixing the fastener against rotation, for example for back-out movement prevention. The spinal plate around the fastener receiving opening is provided with a plurality of slots 131, and the fastener has at least one slot 134 (or vice versa), and the assembly further includes a blocking device 133 that can be placed in the fastener slot 134 aligned with one of the spinal plate slots 131 to fix the orientation around the axis. This measure may be optionally used together with any other approach described in this text.

The plate slots 131, the at least one fastener slot 134 and the blocking device 133 can be designed for allowing the surgeon to decide whether to lock a variation of the angle of the fastener relative to the plate (implant part) in a specific direction or not.

In particular, the at least one fastener slot 134 can be aligned with a plate slot 131 in a manner that a blocking device 133 can be placed at least partially in the fastener slot 134 and at least partially in the plate slot 131. A blocking device 133 placed in this manner can prevent the fastener from a variation of the angle in a plane that includes a longitudinal axis of blocking device 133 and the longitudinal axis of the fastener. In embodiments, the longitudinal axis of the blocking device 133 is the axis along which the blocking device is placed at least partially in the fastener slot 134 and at least partially in the plate slot 131.

In other words, a blocking device 133 placed in this manner can prevent the fastener from a variation of the angle in a plane that includes the axis along which the fastener slot 134 and the plate slot 131 are aligned and that includes the longitudinal axis of the fastener (the axis relative to the plate (implant part)).

The blocking device 133 can be mounted in the plate slot 131 such that it can rotate around its longitudinal axis. Hence, the blocking device 133 can prevent the fastener from a variation of the angle in a plane that includes the longitudinal axis of the blocking device 133 and the longitudinal axis of the fastener but can allow for a rotation of the fastener around the longitudinal axis of blocking device, i.e., a variation of the angle in a plane that includes the longitudinal axis of the fastener and an axis that is perpendicular to the longitudinal axis of the fastener and to the longitudinal axis of the blocking device 133.

A plurality of aligned or alignable fastener slots 134 and plate slots 131 can be used to prevent the fastener from a variation of the angle in a plurality of planes.

For example, two plate slots 131 can be arranged along a longitudinal in-plane axis of the plate (the implant part), wherein one slot extends radially with respect to a center of the fastener receiving opening 11 on each side of the fastener receiving opening 11. Two further plate slots 131 can be arranged accordingly along a transversal in-plane axis of the implant (the implant part). In particular, the longitudinal and transversal in-plane axes are in the same plane given by the plate (the implant part) and are perpendicular to each other. In this case, a blocking device 133 placed in the two plate slots 131 extending along the longitudinal in-plane axis prevent the fastener from a variation in angle in a plane including the longitudinal in-plane axis and the longitudinal axis of the fastener. The same applies for a blocking device 133 placed in the two plate slots 131 extending along the transversal axis.

Instead of locking the variation of an angle of the fastener relative to the plate (implant part), the variation can be limited, for example by choosing a blocking device 133 that is deformable to some extend and/or by placing the blocking device 133 in a manner that hinders (but not prevents) a variation in a specific direction.

There is no need that the locking device 133 is straight or that it is placed in plate slots arranged on opposite sides of the fastener receiving opening 11. For example, the locking device can be Y- or H-shaped. It can be designed, in particular have a size, to extend into the fastener receiving opening, but not bridge it. The plate slot(s) and the fastener slot(s) can be arranged accordingly.

Figure 20:
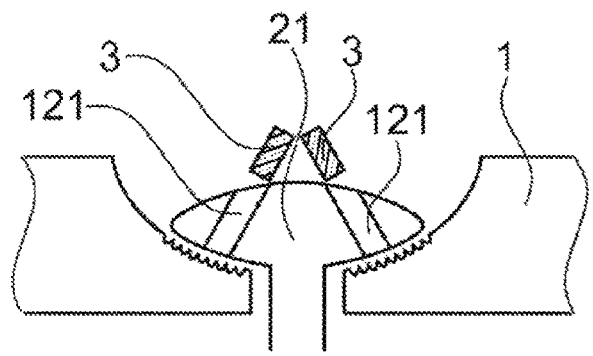

FIG. 20 shows an embodiment similar to the embodiment of FIG. 17, with the difference that the thermoplastic material is not present as cushion or other section of the fastener but is introduced as at least one separate element 3 via through openings 121 (as example of a guidance portion) in the fastener head after placement of the fastener relative to the spinal plate.

Figure 21:
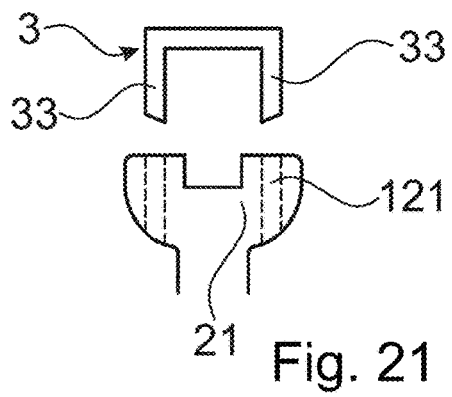
Figure 22:
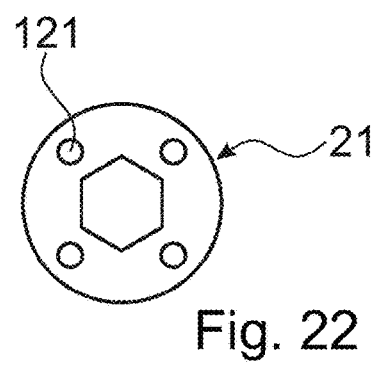
FIGS. 22, 25 and 50 views of a screw head.

A possibility for such separate thermoplastic element 3 is shown in FIG. 21, where the separate element is illustrated to have a plurality of legs 33 each of being inserted into one of the through openings 121, so that the fixation through a plurality of the through openings simultaneously becomes possible. FIG. 22 depicts a top view of an according fastener head.

Figure 23:
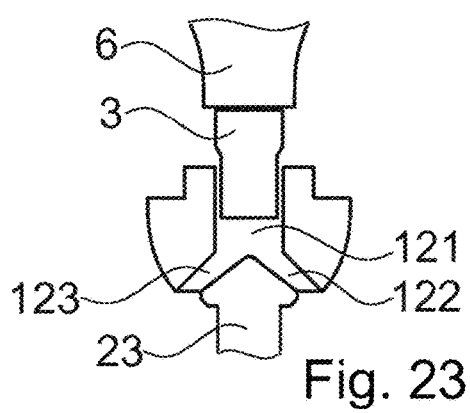

An even further variant is shown in FIG. 23, where the through opening 121 for the thermoplastic element 3 is arranged centrally and includes a plurality of arms 122, 123, whereby a single thermoplastic element is sufficient for fixation at a plurality of spots.

Figure 24:
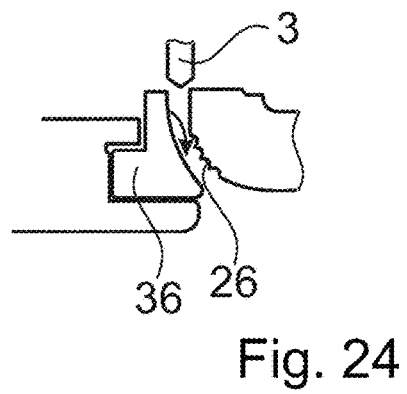

FIG. 24 shows a plurality of principles that can optionally apply; the principles are applicable independent of each other individually or in any possible combination:

the spinal plate 1 has a thermoplastic part 36. The fastener may include structures 26 capable of making a positive-fit connection with liquefied and re-solidified thermoplastic material, and/or it may have thermoplastic material capable of being welded to the thermoplastic material of the spinal plate.

The thermoplastic part 36 (here being a thermoplastic part of the spinal plate; the same applies as an option for a thermoplastic part of the fastener) has a proximal protrusion constituting a reservoir of thermoplastic material that when contacted by the sonotrode during the process is made flowable and flows into the interface region (arrow in FIG. 24).

An optional additional thermoplastic element 3 may be used for providing further thermoplastic material if necessary; the thermoplastic material of the thermoplastic element may be capable of being welded to material of the thermoplastic part.

Figure 18:
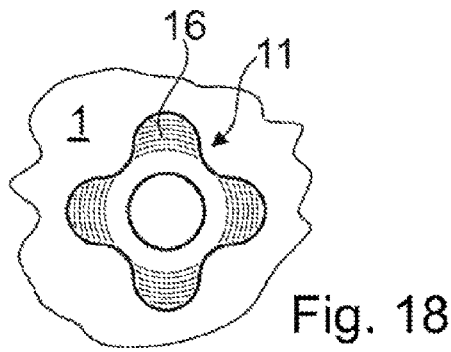
Figure 25:
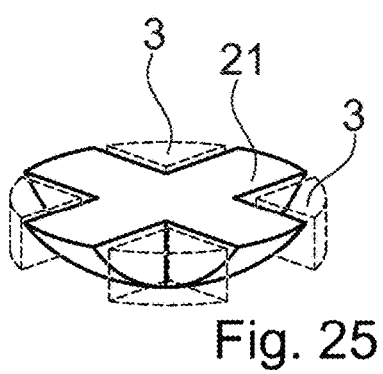
Figure 26:
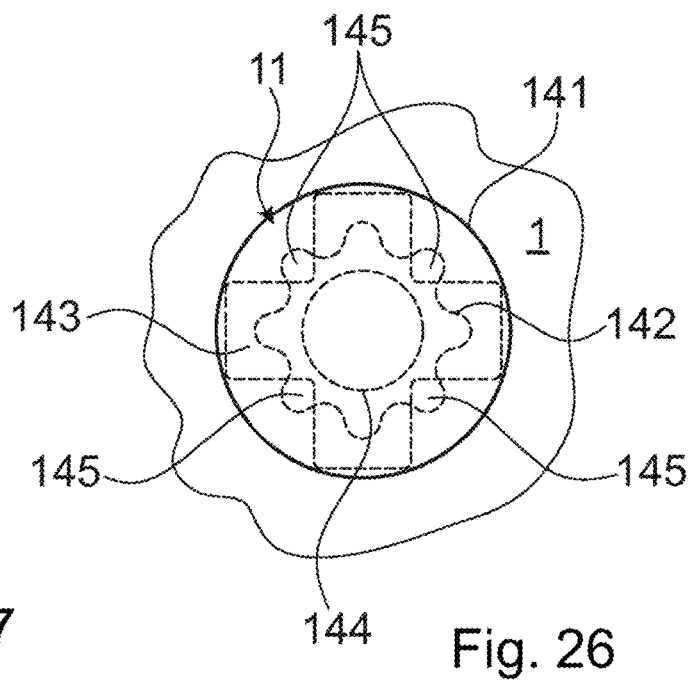

The concept of structures not evenly distributed around the periphery is illustrated in FIG. 18 described hereinbefore. FIG. 25 shows yet another variant in which the fastener head portion 21 has a not round shape (here: a cross shape), and the thermoplastic element(s) 3 are placed in the spaces between the radial protrusions formed by the fastener head 21, as illustrated in FIG. 25. The corresponding spinal plate 1 illustrated in FIG. 26 may be shaped so that the thermoplastic material flows relative to the spinal plate and the fastener in a manner to block the fastener against rotation. In FIG. 26, the solid and dashed lines show the following: 141: outer contour of the fastener receiving opening 11 on the proximal side of the spinal plate; 142: outer contour of the fastener receiving opening 11 on the distal side of the spinal plate (the wall of the opening is shaped for the contour to continuously change from 141 to 142 along the depth of the spinal plate); 143: the outer contour of the fastener head portion; 144: the outer contour of the fastener shaft portion. The shape of the spinal plate and the shape of the head portion 21 together allow portions of the thermoplastic material to flow into spaces—including the spaces 145 axially extending along the interior edges of the head portion 21—that are not rotationally symmetrical and to thereby prevent, after re-solidification rotation of the fastener relative to the spinal plate 1 even if considerable torques may be expected.

Figure 27:
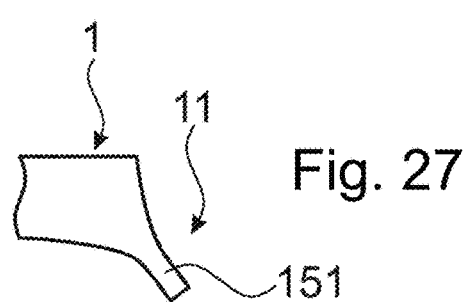

FIG. 27 shows a principle applicable to any embodiment of the invention: the spinal plate, around the fastener receiving opening—has an inwardly (distally) extending collar 151 that enhances the depth along which the spinal fixation plate 1 and the fastener may engage without increasing the overall thickness of the spinal fixation plate. Such inwardly extending collar 151 or other inwardly extending engagement feature may be an option if the clinical situation allows so, for example due to an indentation feature of the bone at the place of the fastening location, as shown in FIG. 2.

In the embodiments of FIGS. 1-26, the fastener receiving opening and the fastener are assumed to be shaped so that the fastener can be inserted relative to the spinal plate at a variable angle, which variable angle is fixed, directly or indirectly, by the thermoplastic material. The following embodiments focus on prevention of 'backout' situations, for example, but not necessarily, with the fastener being a surgical screw, and with the angle between the plate plane and the fastener axis for example being defined by the shapes of the fastener receiving opening and the fastener.

Figure 28:
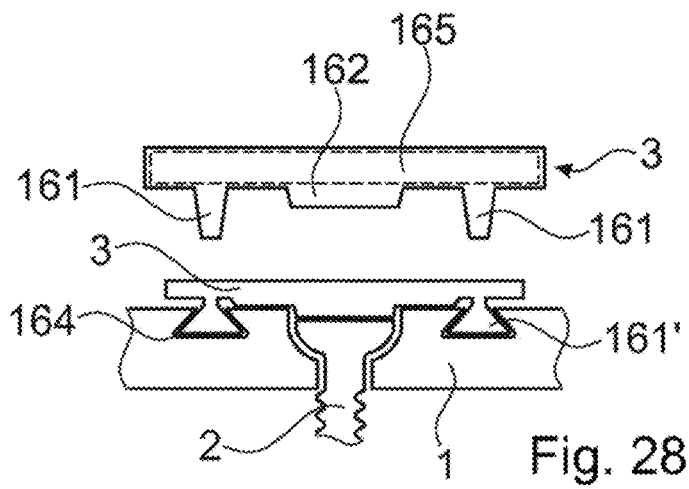

FIG. 28 shows, in the lower part of the figure, a (spinal) plate with a thermoplastic element 3 being configured as plate-shaped backout prevention element. The backout prevention element has a (central) portion proximally of a portion of the fastener 2—in FIG. 28 proximally of the whole fastener 2—so as to prevent backward movements in an axial direction. The backout prevention element has another portion for being secured to the spinal plate 1. To this end, the spinal plate near the fastener receiving opening has at least one securing feature, here in the form of an undercut opening 164 as example of an undercut structure in which flowable material 161' of the backout prevention element may flow to form, after re-solidification, a positive fit connection to the plate 1. The upper part of the figure shows the backout prevention element 3 prior to its being secured to the plate 1. It includes securing protrusions 161 that engage with a structure 164 for the thermoplastic material to flow into the undercut openings 164. A sonotrode (not shown in FIG. 28) acts to press the backout prevention element 3 against the plate while vibrations are coupled into it from proximally until the material of the securing protrusions 161 becomes flowable and flows to at least partially fill the undercut openings 164 as shown in FIG. 28 in the lower part.

Optional features include:

The central portion that is proximally of the fastener has a shallow distally facing protrusion 162, and the head portion of the fastener is correspondingly countersunk.

While in FIG. 28 the backout prevention element is illustrated to consist of the thermoplastic material, this need not be the case. Rather, it may have a non-liquefiable portion. This is illustrated in the upper part of FIG. 28 by an optional non-liquefiable part 165 shown in dashed lines.

Figure 29:
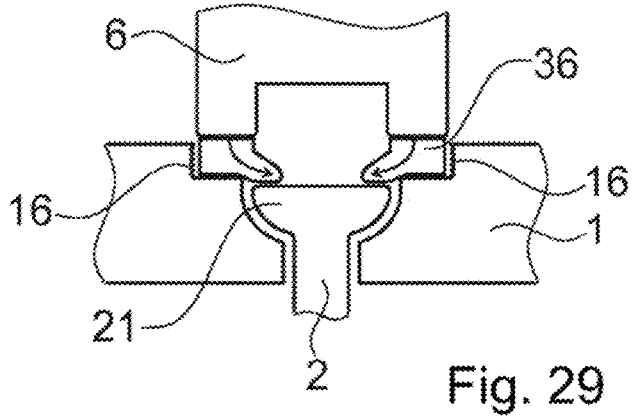
Figure 30:
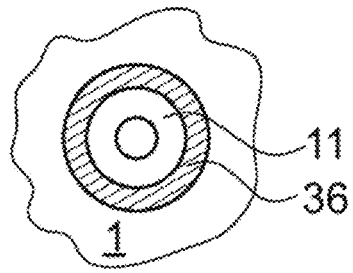

A variant of this embodiment is illustrated in FIGS. 29 and 30. The backout prevention material does not belong to a separate element 3 and is not plate-shaped. Instead, it is present as a ring 36 that may initially belong to the plate 1 and extends around the fastener receiving opening 11. It may especially protrude proximally above the proximal plate plane. The sonotrode 6 acts to deform the ring 36 after the fastener has been implanted, whereby a portion flows in the direction of the arrows in FIG. 29 and after re-solidification lies proximally of the fastener head 21 to prevent a backout movement of the fastener.

The backout prevention material itself is, for example, secured to the spinal plate 1 to which it belongs by a positive fit with structures 16 of the hereinbefore described kind.

A ring shape (or similar) of the kind illustrated in FIG. 29 is also an option if the backout prevention material is provided as separate element like in the embodiment of FIG. 28.

Figure 31:
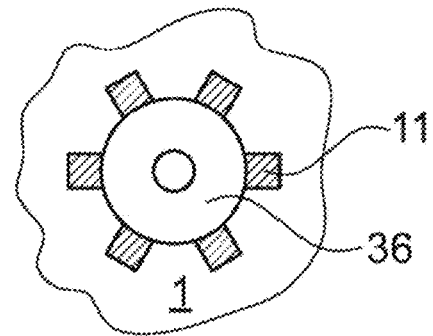

The following variants are possible:

Instead of having a ring shape, the backout prevention material of the plate may have a different shape. In FIG. 31 it is illustrated to include a plurality of discrete pieces arranged around the fastener receiving opening 11.

Figure 32:
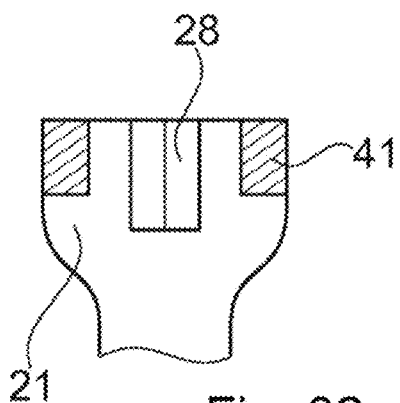

Instead of belonging to the spinal plate 1, the backout prevention material 41 may belong to the fastener as shown in FIG. 32. This pertains to the different shapes, including the shapes of FIGS. 29/30 and FIG. 31.

Figure 33:
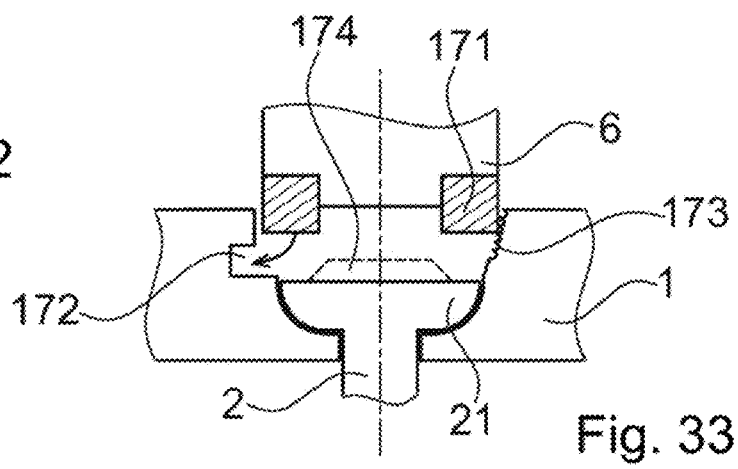

As an even further possibility, the backout prevention material 171 may initially belong to the sonotrode 6, as shown in FIG. 33.

FIG. 33 illustrates on the left side an undercut opening 172 of the spinal plate into which the thermoplastic material 171 may flow to become secured, after re-solidification, to the plate 1.

On the right side, FIG. 33 illustrates a micro-structure 173, for example in the form of open porosity or corrugation, a thread or similar, that may form an undercut with respect to axial directions, to secure the thermoplastic material 171, after re-solidification, to the plate 1. Such structures are options also for the embodiments with the backout prevention material belonging to the fastener or the plate or being provided as separate element.

FIG. 33 further illustrates an optional material guiding protrusion 174 of the fastener that ensures a flow sidewards into the undercut opening(s) 172, 173.

Figure 34:
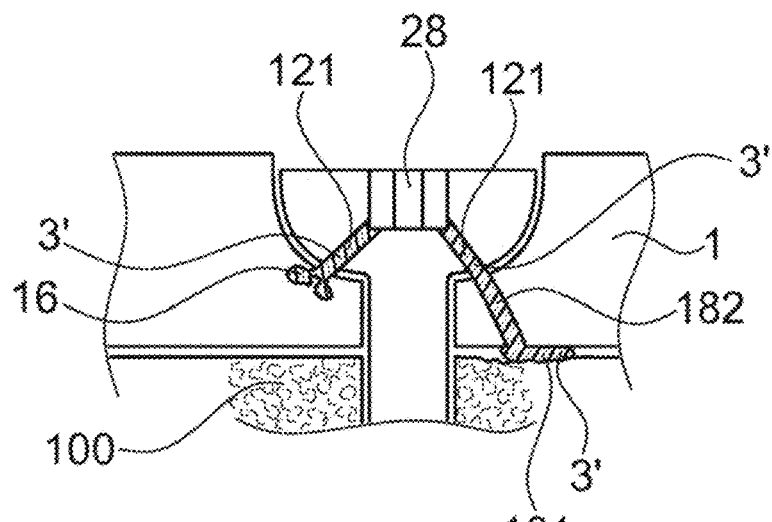

In the embodiment of FIG. 34, the fastener head includes at least one through opening 121 through which a thermoplastic element may be introduced and from which thermoplastic material can be dispensed towards distally—similarly to FIG. 20. On the left side, the thermoplastic material pressed out of the through opening is illustrated to penetrate into undercut structures 16 of the spinal plate to yield a backout fixation (fixation against movements of the fastener into proximal direction), whereas on the right side, the thermoplastic material is dispensed through an aligned through opening 182 in the spinal plate to distally of the spinal plate (material portions 3') to yield, after re-solidification, a blind rivet head 181 like positive-fit connection.

Figure 35:
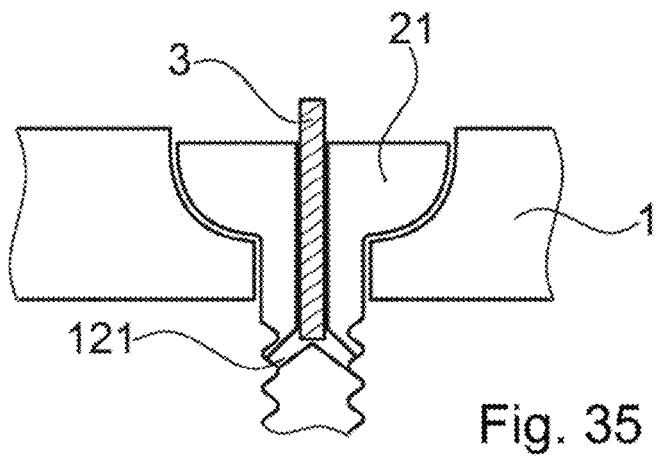

The embodiment of FIG. 35 is based on the principle described, for example, in WO 2011/054124, namely the fastener having a through opening 121 through which thermoplastic material from a thermoplastic element is pressed into surrounding bone tissue to yield, after re-solidification, a positive fit connection with the bone tissue.

Figure 36:
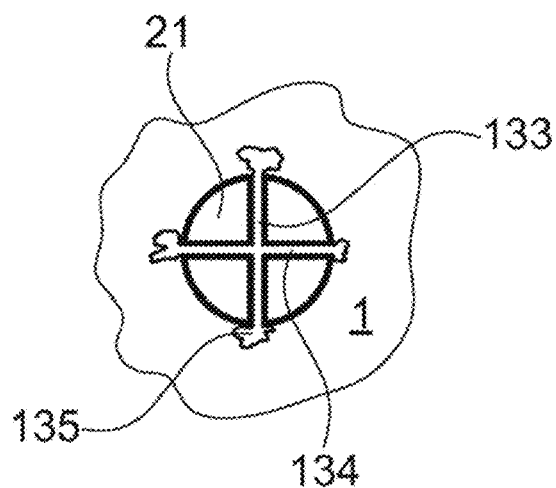

The embodiment of FIG. 36 includes a thermoplastic element 133 that is placed in an adapted structure 134, here formed by a cross-shaped groove in the proximal end face of the fastener's head portion 21. End portions 135 of the thermoplastic element are pressed, by a vibrating sonotrode, into structures of the spinal plate near the fastener receiving opening to be, after re-solidification a bond to the spinal plate. In contrast to the embodiment of FIG. 28, the backout prevention is not primarily due to a fixation against movements in a rearward (towards proximally) axial direction, but due to a fixation against rotation around the axis, which fixation will especially be advantageous if the fastener has an outer thread.

Figure 37:
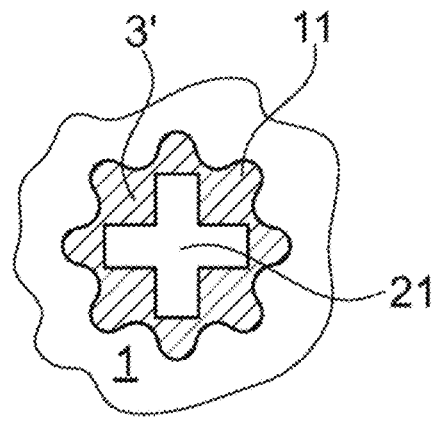

The embodiment of FIG. 37, finally, is based on a similar principle as the one of FIG. 26, with a fastener head portion 21 that is not rotationally symmetrical and also with a fastener receiving opening that is not rotationally symmetrical. In the embodiment of FIG. 37, the not rotationally symmetrical shape of the fastener receiving opening extends to the proximal surface of the spinal plate, whereby in at least one plane—and for example along the full thickness of the plate—both, the fastener head portion and the fastener receiving opening are not rotationally symmetrical, whereby re-solidified thermoplastic material 3' stemming from a thermoplastic element and/or possibly, as described hereinbefore, from thermoplastic portions of the plate, the fastener and/or the sonotrode, impedes any rotation of the fastener head relative to the plate.

FIGS. 38-54 show further embodiments of the implant system that are capable for "backout" prevention. In particular, FIGS. 38-54 show various embodiments of the securing element 3 before mechanical activation or after resolidification, this means the securing element 3 that is a backout prevention element in such embodiments and that is configured to be connected to the plate and to block the fastener against escaping towards proximally relative to the plate is shown before and after its deformation.

Some of the embodiments shown in FIGS. 38-54 are further capable to provide additional stability against rotation of the fastener around the fastener axis or can be adapted to provide such additional stability, in particular by breaking the rotational symmetry of the structures interacting with the thermoplastic material. This can be done by designing said structures in a non-continuous manner, for example by restricting their expansion and/or by interrupting them, e.g. by walls dividing said structures in distinct compartments.

The embodiments shown in FIGS. 38-54 (and also a plurality of the embodiments shown in FIGS. 1-37) are implanted with a method including the steps of placing the spinal plate relative to the bone tissue and anchoring the fastener implant in the bone tissue, causing energy to impinge on thermoplastic material until a flow portion thereof becomes flowable and flows relative to the spinal plate and the fastener, stopping the energy transfer, and causing the thermoplastic material to re-solidify, whereby the fastener is fixed relative to the spinal plate by the thermoplastic material.

Figure 38:
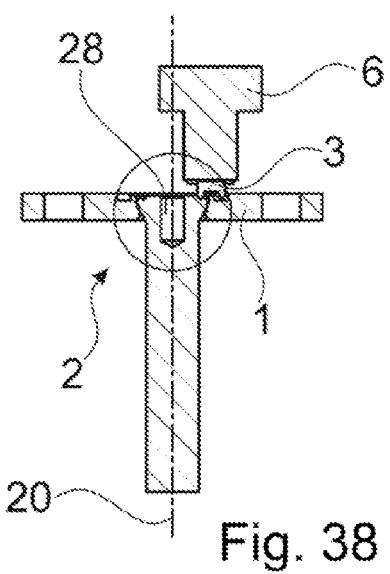

FIG. 38 shows exemplarily the situation at the beginning of the step of causing energy to impinge on the thermoplastic material. In the embodiment shown, the energy is generated by the sonotrode 6.

In the following, the region encircled in FIG. 38 is shown when not otherwise stated.

Figure 39:
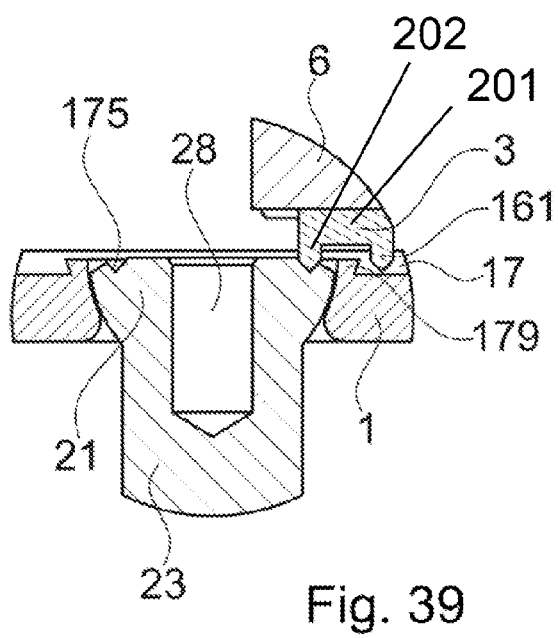

FIG. 39 shows an initial configuration for a connection between the fastener 2 and the plate 1 that is caused by the fastener head 21 including a groove 175.

The plate 1 includes a securing structure of the kind shown in FIG. 5, 7, 16 or 28 for example, in order to fix the thermoplastic material to the plate 1 after the step of causing the thermoplastic material to re-solidify.

The groove 175 and the securing structure 17 are essentially continuous, this means the groove 175 forms a closed loop and the securing structure 17 forms a closed loop. Further, the groove 175 and the securing structure 17 run essentially parallel to each other.

The securing element that is a thermoplastic element 3 in the embodiment of FIG. 39 is separate from the plate 1 and the fastener 2 and it is designed for establishing a local connection between the fastener 2 and the plate 1. In other words, the thermoplastic element 3 is of the kind that it does not encompass the full periphery of the fastener head 21 but only a rather small part of it. Accordingly, the sonotrode 6 can be applied locally to the thermoplastic element 3 as shown in FIG. 38.

The thermoplastic element 3 has a bridge portion 201 and includes a first protrusion 161 that is arranged such that it can engage with a first structure 17 and a second protrusion 202 to be positioned in a second structure, here the groove 175.

The groove 175, the securing structure 17 and the thermoplastic element 3 can be designed such that the first and second protrusions can engage with the groove 175 and the securing structure 17 respectively independent of the angle of the fastener 2 relative to the plate 1.

Such designs of the groove 175, the securing structure 17 and the thermoplastic element 3 allow for a maximal scope of action concerning the number of thermoplastic elements 3 used and concerning its/their positioning.

The groove 175 is designed such that liquefied thermoplastic material can flow in the groove 175. In other words, the liquefied thermoplastic material can be guided by the groove 175 in a predefined direction.

This allows for the generation of a clamp-like backout prevention element that connects the fastener 2 to the plate 1. The clamp-like backout prevention element includes re-solidified thermoplastic material that has flown along the groove 175 and an anchor in the securing structure 17 of the plate 1 at the initial position of the thermoplastic element. Further, a clamp-like backout prevention element can be generated independent of the angle of the fastener 2 relative to the plate 1.

In the embodiment shown in FIG. 39, the securing structure 17 is defined by a surrounding wall having a reduced height 179 towards the fastener receiving opening 11. This reduced height 179 makes sure that the sonotrode 6 does not get in touch with the mouth forming the proximal end of the fastener receiving opening 11. Thereby, the reduced height 179 enables the formation of a bridge between thermoplastic material arranged in the securing structure 17 after re-solidification and thermoplastic material arranged in the groove 175 after re-solidification.

Figure 40:
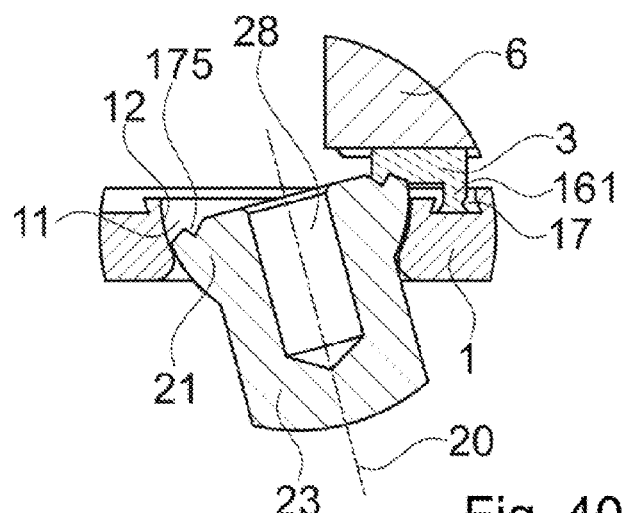

FIG. 40 shows the situation during the step of applying energy to the thermoplastic material and for a fastener 2 having a fastener axis 20 that runs at an angle to the normal defined by the distal surface portion of the plate 1 surrounding the fastener receiving opening 11, this means the fastener axis 20 is not parallel to the longitudinal axis of the receiving opening 11.

Distal portions of the protrusions 161 of the thermoplastic element 3 have become flowable. The flowable portions flow along the groove 175 and fill the securing structure 17, respectively.

Figure 41:
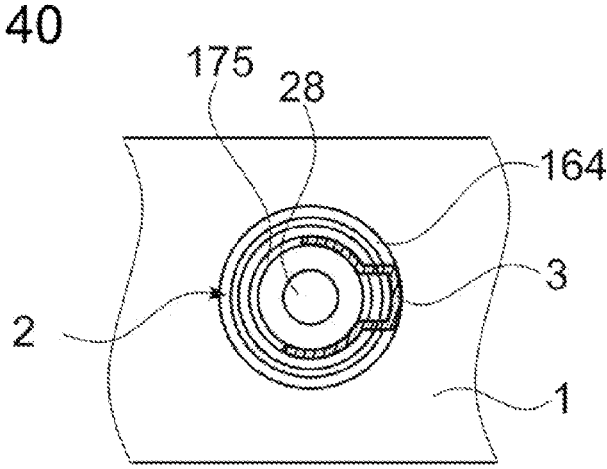

FIG. 41 shows the situation after re-solidification of the thermoplastic material and when one thermoplastic element 3 is used only. The clamp-like backout prevention element that has been generated can be seen.

The volume of thermoplastic material and/or the design of the groove 175 can be chosen to design the backout prevention element. In particular, the volume of thermoplastic material and/or the design of the groove 175 can be such that the thermoplastic material fills a portion of the groove 175 only, such that the thermoplastic material forms a closed shape defined by the groove 175, or such that the thermoplastic material flows into open space and/or structures neighboring the groove 175, for example securing structures in the plate 1.

FIG. 41 shows the situation when the volume of thermoplastic material and the design of the groove 175 is chosen such that the thermoplastic material fills a portion of the groove 175 only. However, one can envisage to use at least one further thermoplastic element 3 of the kind shown in FIGS. 40 and 41 in order to form at least two clamp-like backout prevention elements or a backout prevention element that forms a closed loop of thermoplastic material having at least two anchoring locations in the plate 1.

The thermoplastic material, the design of the groove 175, the volume of the thermoplastic material and/or the number of thermoplastic elements 3 can be chosen to secure the fastener against a variation of the angle relative to the plate or for allowing such a variation of the angle.

In particular, the clamp-like backout prevention element whose properties are essentially given by the thermoplastic material and its shape given by the design of the groove 175, the volume of the thermoplastic material and the number of thermoplastic elements 3 can be such that the backout prevention element is deformable. In particular, it can be deformable in a manner to allow for a change in angle of the fastener 2 relative to the plate.

Figure 42:
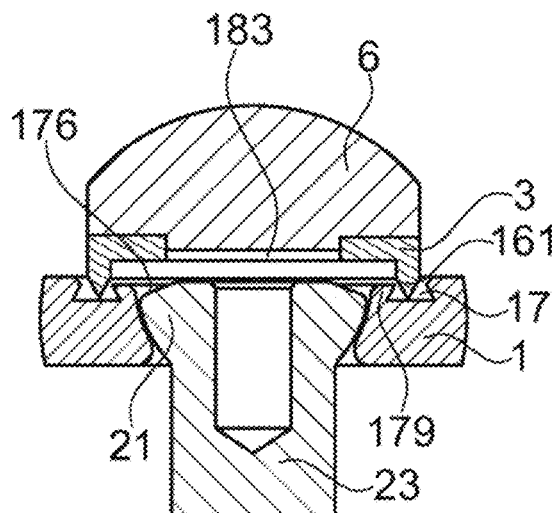

FIG. 42 shows an initial configuration for another system resulting in a connection between the fastener 2 and the plate 1 including an element for backout prevention.

The configuration shown can either lead to thermoplastic material forming a connection between the fastener 1 and the plate 2 (FIG. 43a) or to a securing element that does not form such a connection or forms such a connection at a maximal angle between fastener 2 and plate 1, only (FIG. 44a). It depends on the design of the thermoplastic element/the securing element 3 and possibly of the design of a coupling-out face 183 of the sonotrode 6 and/or the design of the proximal surface of the plate 2 and/or the proximal surface of the fastener head 21 which of the two embodiments is realized.

In the embodiment shown, the thermoplastic element/securing element 3 is fixed to the sonotrode 6 before implantation. Alternatively, the sonotrode can include the coupling-out face 183 and the thermoplastic element/securing element 3 can be designed in a manner that the thermoplastic element 3 can engage with the sonotrode 6.

The plate 1 includes the securing structure of the kind shown in FIG. 5, 7, 16 or 28 for example. Further, the thermoplastic element/securing element 3 includes a protrusion 161 that is arranged such that it can be positioned in the securing structure 17. This simplifies positioning of the thermoplastic element/securing element 3 and the sonotrode as well as simplified handling of the sonotrode during the method.

The securing structure 17 can include the reduced height 179 towards the fastening receiving opening 11 that enables the formation of a bridge bridging a gap between the plate 1 and the fastener 2.

The proximal surface of the fastener head 21 declines in a radial direction (radial with respect to the fastener axis 20). The declining portion 176 can be designed to contribute to the formation of the backout prevention element (as shown exemplarily in FIGS. 43a and 45a) or for an areal contact between the fastener 2 and the backout prevention element at a maximal angle between fastener 2 and plate 1 (exemplarily shown in FIG. 45b).

Figure 43A:
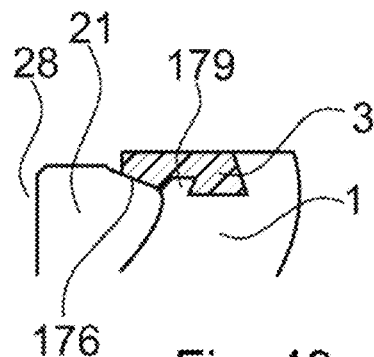
Figure 43B:
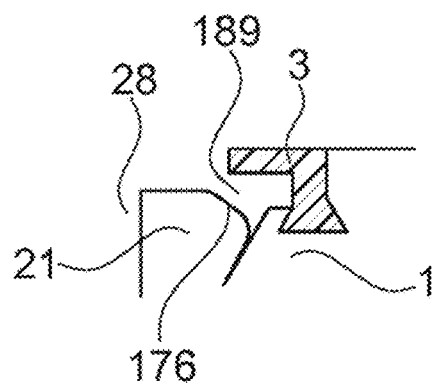

FIGS. 43a and 43b show two possible embodiments established after resolidification of the thermoplastic material.

The connection according to FIG. 43a is formed by the protrusion 161 filling the securing structure 17. Further, portions of the thermoplastic element/securing element 3 have flown into space made available by the declining portion 176 of the proximal surface of the fastener head 21.

The overall shape of the re-solidified thermoplastic material is given by the shape of the securing structure 17 (including the reduced height 179), the embodiment of the declining portion 176, and the shape of the coupling-out face 183 of the sonotrode 6.

In principle, the connection according to FIG. 43a secures the fastener 2 against a variation of the angle of the fastener relative to the plate 2. However, one can envisage choose a thermoplastic material that is deformable in order to allow for such a variation.

The deformed thermoplastic element/securing element 3 according to FIG. 43b is formed includes the protrusion 161 filling the securing structure 17, wherein a proximal end of the thermoplastic element/securing element 3 is not deformed during the process or deformed in a manner that it includes a proximal head.

In this embodiment, the backout prevention element is separated from the fastener 2 by free space 189 immediately after implantation. In other words, the blackout prevention element does not prevent the fastener to change its angle with respect to the plate—at least not before a maximal change in angle has occurred.

Further, the backout prevention element generated, this means the deformed thermoplastic element/securing element 3, does not form a connection between the fastener 1 and the plate, at least for the angle between the fastener 2 and the plate 1 shown in FIG. 43b.

Figure 45A:
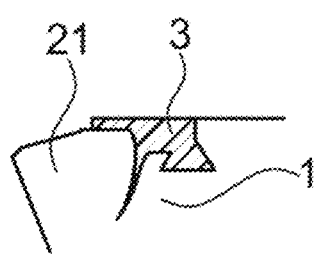
Figure 45B:
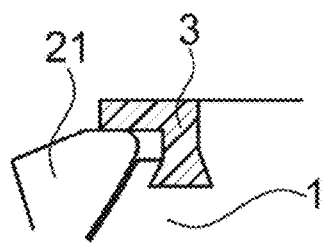

FIG. 45b shows exemplarily the situation when a maximal change in angle between the fastener 2 and the plate 1 has occurred.

Figure 44:
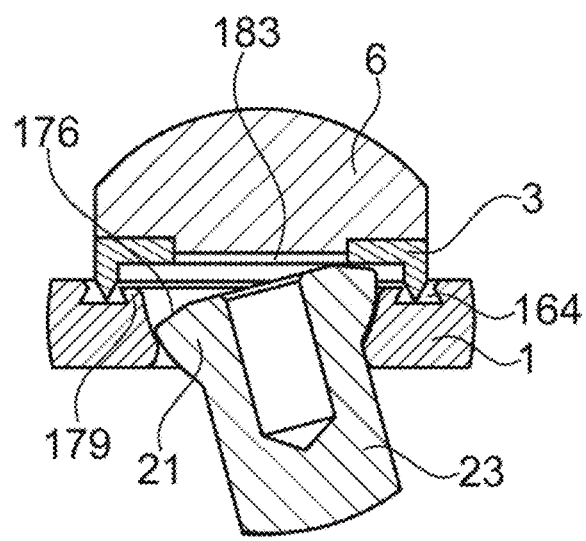

FIGS. 44 and 45a/b show the situation when the fastener 2 is anchored in bone tissue under an angle other than 90 degree with respect to the plate 1.

FIG. 44 shows the initial configuration. FIGS. 45a/b shows the situation at the right connection location shown in FIG. 44 after re-solidification of the thermoplastic material.

According to the exemplary embodiment shown in FIG. 44, the coupling-out face 183 is adapted to the shape of the proximal surface of the fastener head 21 in a manner that the thermoplastic material includes a portion arranged on the proximal surface of the fastener head 21 after re-solidification. In other words, the coupling-out face 183 is adapted to the shape of the proximal surface of the fastener head 21 in a manner that the thermoplastic material is not pressed away, not completely pressed away at least, from the proximal surface of the fastener head 21 during the method.

FIG. 45a shows the shape of the thermoplastic element/securing element 3 after re-solidification of the thermoplastic material.

Again, the shape of the coupling-out face 183 and/or of the reduced height 179 can allow the formation of a bridge between thermoplastic material in the securing structure 17 and thermoplastic material that has flown into said opening.

A variation of the angle of the fastener 2 relative to the plate 1 is only possible if the thermoplastic material, possibly in combination with the shape of the backout prevention element generated, is chosen in a manner that the backout prevention element deforms under forces that are generated during healing and/or fusion.

In contrast to FIG. 45a, FIG. 45b shows a backout prevention element that defines a maximal deviation of the fastener axis from to plate normal (the axis of the fastener receiving opening 11). Such a backout prevention element allows for a variation in angle between the fastener 2 and the plate 1 without need for deformation of the backout prevention element.

In the embodiment of FIGS. 46-49, the thermoplastic element/securing element 3 or the thermoplastic elements/securing elements is/are pre-assembled with the plate 1.

The thermoplastic element(s) are arranged on the plate 1 in a manner that the positioning of the fastener in the plate 1 is unaffected by the thermoplastic element(s) 3.

For example, the thermoplastic element 3 can have the shape of a ring with an inner diameter that corresponds to, or is larger than, a proximal diameter of the fastener receiving opening 11.

Figure 46:
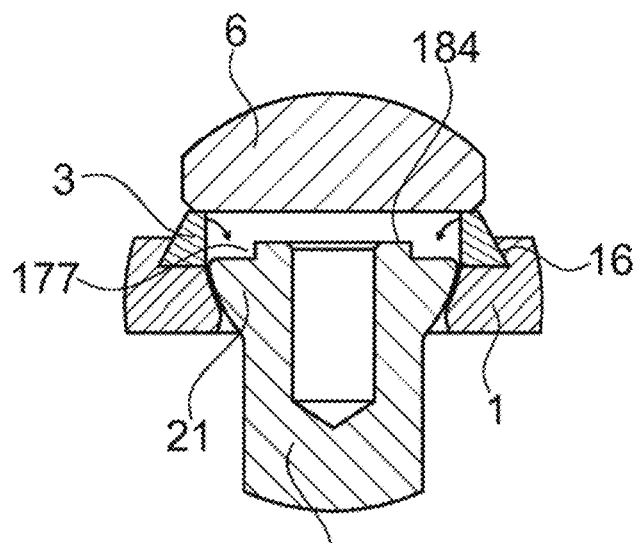
Figure 47A:
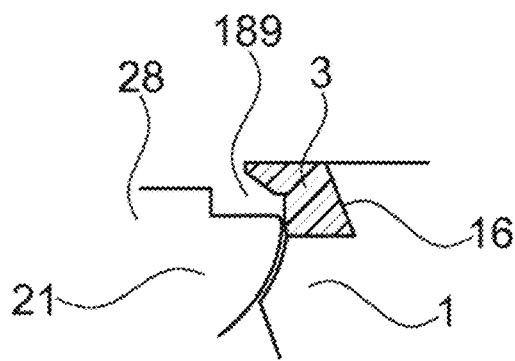

Two possible configurations of backout prevention can be established starting from the initial configuration shown in FIG. 46:

FIG. 47a shows the formation of a head that is separated by free space 189 from the fastener 2. This configuration allows for backout prevention without affecting a variation in angle between the fastener 2 and the plate 1.

Figure 47B:
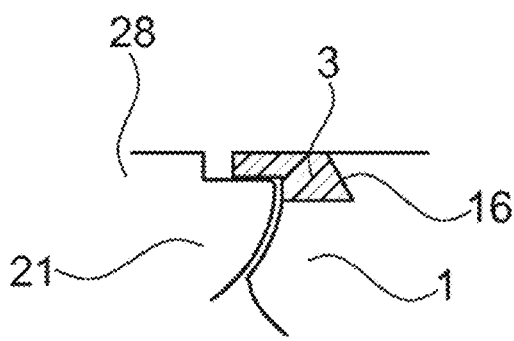

FIG. 47b shows a formed backout prevention element that is able for securing the fastener 2 against a variation in angle relative to the plate 1, too. However, the thermoplastic material can be chosen that it is able to deform under forces generated during healing and/or fusion.

In the embodiment shown, a recess 177 is arranged at the periphery of the proximal surface of the fastener head 21. A not recessed region 184 of the proximal surface of the fastener head 21 can be capable to prevent a further movement of the sonotrode 6 in distal direction.

A backout prevention element that prevents the fastener axis from changing its angle relative to the plate plane by a movement in a specific direction can be established if two thermoplastic elements/securing elements 3 that extends over a small range of the periphery of the fastener receiving opening 11 only and that are preassembled on the proximal surface of the plate 1 on opposite sides of fastener receiving opening 11 are used. The specific direction is then any direction that is in the plane including the fastener axis and the two thermoplastic elements 3.

Figure 48:
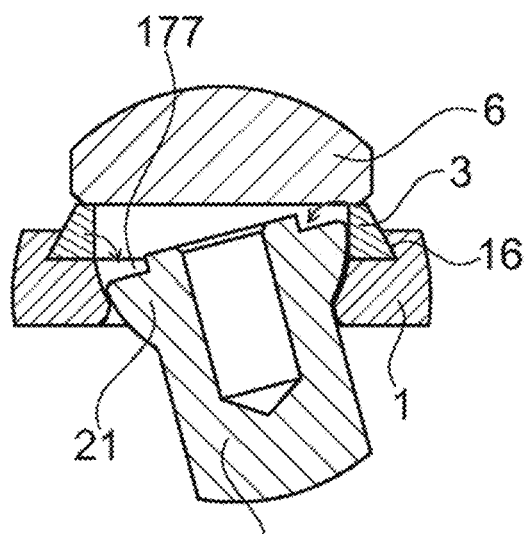

FIG. 48 shows the initial configuration when the fastener axis 20 runs at an angle to the normal defined by the distal surface portion of the plate 1 surrounding the fastener receiving opening 11, this means the fastener axis 20 is not parallel to the longitudinal axis of the receiving opening 11.

Figure 49:
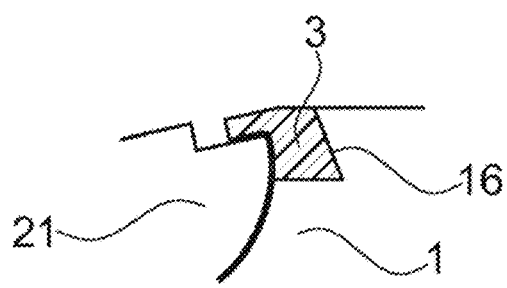

The designs of the fixation structure 16, the recess 177 and the thermoplastic element/securing element 3 allow for the formation of the element that causes prevention from back-out movement. A corresponding backout prevention element is shown in FIG. 49.

Again, the backout prevention element generated does not prevent a variation of the fastener axis towards smaller angles with respect to the normal of the distal surface of the plate (or the longitudinal axis of the receiving opening).

With respect to larger angles (and if a non-deformable thermoplastic material is chosen, this means hard thermoplastic material as discussed above), the backout prevention element generated hinders a variation caused by a movement of the fastener axis in a plane including the portion of the backout prevention element being in contact with the fastener.

In a group of embodiments, the securing structure, for example of the kind described with respect to FIG. 5, 7, 16, 28 or 33, can be arranged at the wall 12 of the fastener receiving opening 11 and the fastener head 21 can be equipped to guide thermoplastic material that is arranged or positioned on the distal end of the fastener head 21 into the securing structure 17.

Figure 50:
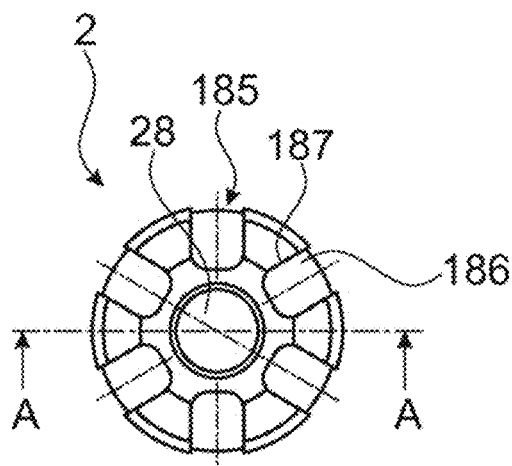
Figure 51:
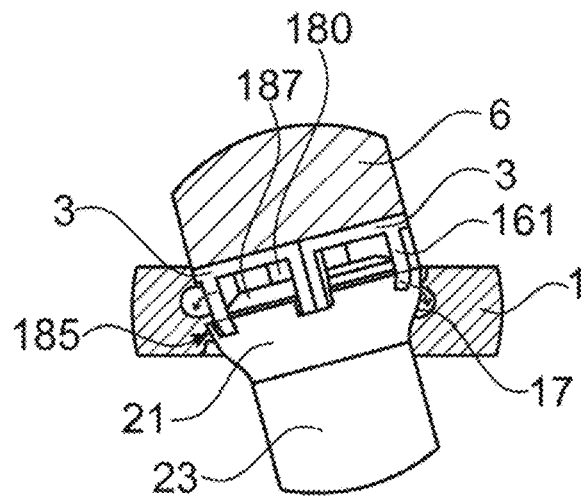
Figure 52:
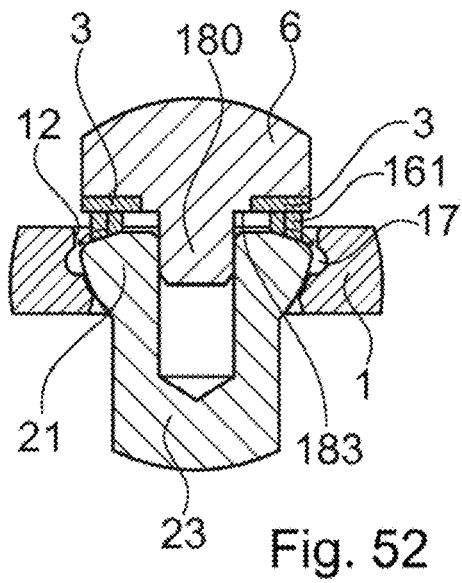
Figure 53:
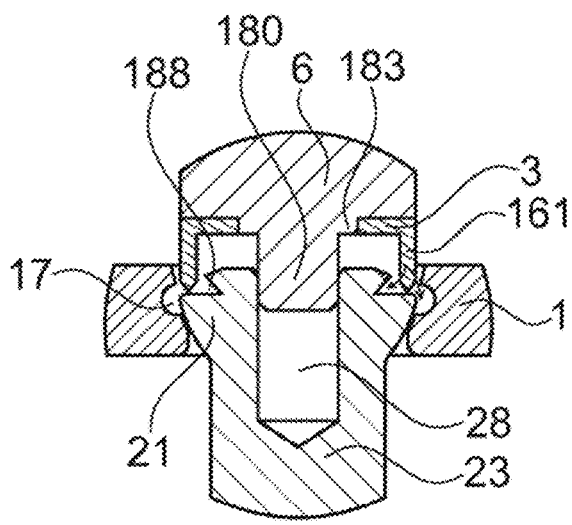
Figure 54:
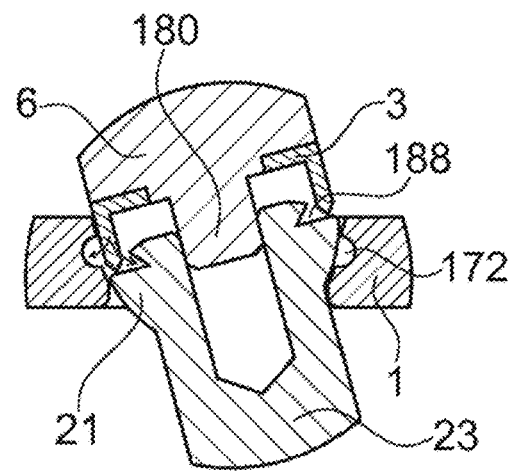

For example, the distal end of the fastener head 21 can be of the kind shown in FIGS. 50-52 or of the kind shown in FIGS. 53 and 54.

FIG. 50 shows a top view of an exemplary fastener head 21 that is capable to guide thermoplastic material into the securing structure 17 arranged at the wall 12 of the fastener receiving opening 11. In the embodiment shown, the fastener head 21 includes a plurality of recesses in the shape of channels 185 that are open towards the radial periphery of the fastener head 21.

The channels 185 are arranged essentially along a radial direction (radial with respect to the fastener axis 20). However, this is an optional feature only.

The channels 185 include openings that are evenly distributed around the periphery of the fastener head 21. However, this is an optional feature only.

FIG. 51 shows a 3D-view of the fastener 2 of FIG. 50 and a sectional view of the plate 1. The fastener 2 is shown after positioning in the fastener receiving opening 11. The situation with the fastener axis 20 running at an angle to the normal defined by the distal surface portion of the plate 1 surrounding the fastener receiving opening 11, this means the fastener axis 20 is not parallel to the longitudinal axis of the receiving opening 11, is shown.

The shape of the channels 185 at their open ends is designed to allow the flow of liquefied thermoplastic material from the channels 185 into the securing structure 17 independent of the orientation angle of the fastener 2 relative to the plate 1. In other words, the shape of the channels 185 at their open ends is designed to enable the flow of liquefied thermoplastic material from the channels 185 into the securing structure 17 over the whole range of possible angles between fastener axis 20 and plate 1.

In the embodiment of FIG. 51, this ability of the channels 185 is realized by channels having a bottom 186 that is—at least in the region of their open ends—at a more distal position than a proximal end of the securing structure 17 and an edge 187 defining a distal end of the channel that is—at least partly—at a more proximal position than a distal end of the securing structure 17.

In particular, the arrangement of the securing structure 17 and the design of the channels 185 is such that the relative position of the channel bottom 186 and the proximal end of the securing structure 17 on the one hand and the channel edge 187 and the distal end of the securing structure 17 on the other hand keeps true for the whole range of possible angles between fastener axis 20 and plate 1.

The thermoplastic element 3 can include a plurality of protrusions 161 designed for engaging with the plurality of channels 185. In particular, the thermoplastic element 3 can be adapted to the design and/or the arrangement of the channels 185. However, the exemplary embodiment of FIG. 51 (and FIGS. 52-54) also works with a ring-like thermoplastic element 3 instead of a cap-like thermoplastic element 3 or with a cap-like element that has no specific distal geometries being adapted to the channels 185.

The backout prevention element generated by the fastener 2 and plate 1 shown in FIGS. 50-52 is an example of backout prevention elements that secure the fastener against any variation of the fastener axis relative to the plate 1.

Further, the backout prevention element generated can prevent the fastener 2 from a rotation around the fastener axis.

FIG. 52 shows a cross-sectional view through the plate 1 and the fastener 2 along the plane A-A of FIG. 50.

The sonotrode 6 includes a protrusion 180 that is capable to engage with the tool opening 28. This engagement enables application of the sonotrode in an off-axis configuration, this means in a configuration in which a longitudinal axis of the sonotrode 6 is not parallel to the normal of the plane 1.

Further, the protrusion 180 can be equipped for causing a rotational movement of the fastener 2 around the fastener axis. In particular, the sonotrode 6 can be equipped for acting as a screw driver.

In the embodiment shown, the sonotrode 6 includes a coupling-out face 183 that is capable to guide the thermoplastic element(s) during the method. For example, the thermoplastic elements 3 includes a plurality of protrusions arranged distally of a ring-shaped body of the thermoplastic element 3. In this embodiment of the thermoplastic element 3, the coupling-out face 183 can include a ring-shaped recess that is adapted to the ring-shaped body of the thermoplastic element 3.

FIGS. 53 and 54 show a further embodiment of the fastener head 21 that is capable to guide thermoplastic material into the securing structure 17 arranged at the wall 12 of the fastener receiving opening 11.

FIG. 53 shows a cross-sectional view of the fastener 2 inserted in the fastener receiving opening 11 for the case of the fastener 2 being aligned along the normal defined by the distal surface portion of the plate 1 surrounding the fastener receiving opening 11, this means the fastener axis 20 is parallel to said normal and/or the longitudinal axis of the receiving opening 11.

FIG. 54 shows the situation with the fastener axis 20 running at an angle to the normal defined by the distal surface portion surrounding the fastener receiving opening 11, this means the fastener axis 20 is not parallel to the longitudinal axis of the receiving opening 11.

Again, the fastener 2 includes a tool opening 28 that is adapted to the protrusion 180 of the sonotrode in a manner that the sonotrode is guided in off-axis configuration. Further, the tool opening can be adapted to the protrusion 180 in a manner to apply a torque to the fastener 2 via the sonotrode 6.

The embodiment according to FIGS. 53 and 54 distinguishes from the embodiment according to FIGS. 50-52 in that the fastener 2 has an undercut portion 188, for example of the kind described with respect to FIG. 9. However, the undercut portion 188 of FIGS. 53 and 54 is designed to guide liquefied thermoplastic material to the securing structure 17.

For example, this can be done by the undercut portion 188 having a region in which a bottom of the undercut portion 188 is more distal than the proximal end of the securing structure 17 and a region in which an edge of the undercut portion 188, the edge defining a proximal end of the undercut portion 188, is more proximal than the distal end of the securing structure 17.

In particular, the arrangement of the securing structure 17 and the design of the undercut portion 188 is such that said relative position of the bottom of the undercut portion 188 and the proximal end of the securing structure 17 on the one hand and the edge defining the proximal end of the undercut portion 188 and the distal end of the securing structure 17 on the other hand keeps true for the whole range of possible angles between fastener axis 20 and plate 1.

In the case of the connection region shown on the right of FIG. 54, said relative arrangement of the securing structure 17 and the undercut portion 188 is present at a region of the undercut structure 188 that is in a plane behind and/or in front of the cross-sectional plane shown in FIG. 52.

The thermoplastic element 3 can have at least one protrusion that is arranged such that liquefied thermoplastic material flows into the undercut structure 188. In particular, it can be arranged such that it gets in contact with a portion of the fastener head 21 that forms the bottom of the undercut structure 188.

The undercut structure 188 can run along the whole periphery of the fastener head 21. However, it can also be restricted to regions of the fastener head 21.

The backout prevention element generated by fastener 2 and plate 1 shown in FIGS. 53 and 54 is a further example of backout prevention elements that secure the fastener against any variation of the fastener axis relative to the plate 1. However, the capability of the backout prevention element to prevent the fastener 2 from a rotation around the fastener axis is reduced compared to the embodiment generated by the fastener 2 and plate 1 shown in FIGS. 50-51. This is due to use of securing structures that are rotationally symmetric.

Figure 55:
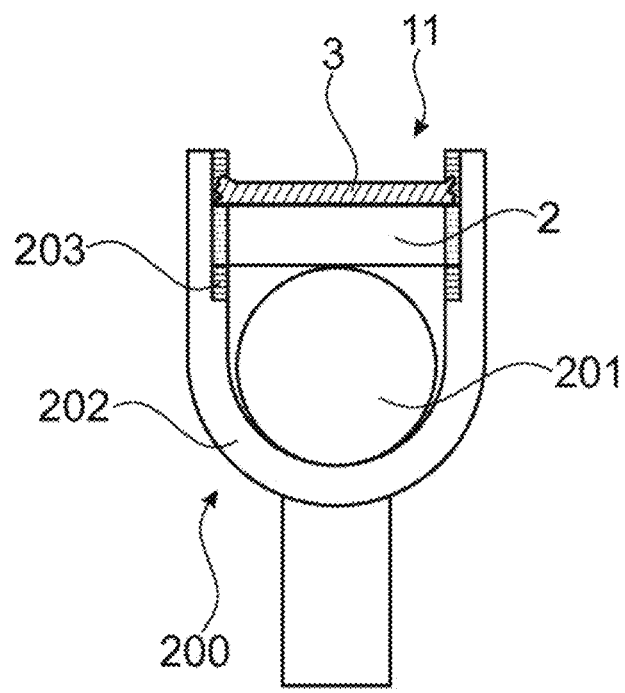
FIGS. 55-63 schematics of exemplary implant systems according to the invention.

FIG. 55 shows a sectional view of an implant system being a spine stabilization system. The spine stabilization system of which the sectional view is shown includes at least two pedicle screws 200 and a stabilization (fixation) rod 201, wherein at least one pedicle screw is anchored in each vertebra to be stabilized and the rod 201 can be mounted to a proximal end of each pedicle screw.

The spine stabilization system shown includes a pedicle screw 200, a fixation element being a rod 201 and a fastener being a setscrew 2. The pedicle screw 200 includes a tulip 202 with an inner thread 203. The setscrews 2 have an outer thread. The tulip 202 forms the fastener receiving opening 11.

The pedicle screw 200 can be considered as a first implant part and the rod 201 can be considered as a second implant part.

The rod 201, the tulip 202 and the setscrew 2 are designed in a manner that the rod 201 can be positioned in the tulip 202 and that the rod 201 can be clamped between the setscrew 2 and the tulip 202. In the embodiment shown, the clamping force is screwing the setscrew 2 into the tulip 202 via the fastening receiving opening 11.

The spine stabilization system shown includes further a securing element 3 that can be inserted into the fastening receiving opening 11 and positioned proximally of the setscrew 2.

The securing element 3 and the tulip 202 are equipped for the securing element 3 to be mounted on the tulip 202 in a manner that the setscrew cannot move in a proximal direction. In other words, the mounted securing element 3 prevents the setscrew 2 from a movement that reduces the clamping force.

Figure 56:
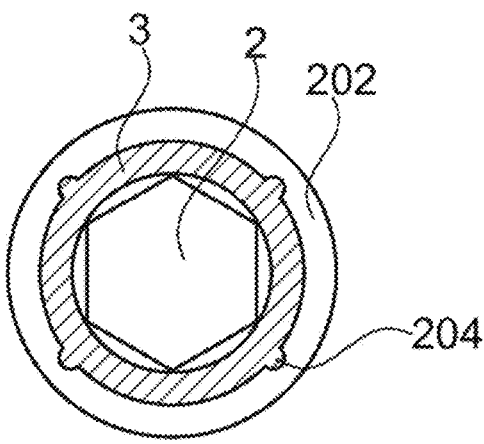

FIG. 56 shows an exemplary embodiment of a securing element 3 and a tulip 202 equipped for preventing the setscrew 2 to move in a proximal direction.

It goes without saying that the concept shown in FIG. 56 can be used or adapted for any other implant systems including a securing element (thermoplastic element as the case may be), an implant part having a fastener receiving opening and a fastener in a configuration comparable to the configuration shown in FIG. 56.

In the exemplary embodiment shown in FIG. 56, the tulip 202 (implant part) includes axial openings 204. The axial openings 204 are arranged in a manner that liquefied thermoplastic material of the securing element positioned proximally of the fastener 2 can flow into. The axial openings 204 are designed such that a positive-fit connection between the securing element 3 and the tulip 202 is formed after re-solidification of the thermoplastic material, said positive-fit connection being with respect to a rotation around the longitudinal axis of the fastener receiving opening 11 (of the inner thread 203, in the embodiment shown).

The tulip 202 (implant part) further includes a structure that forms a positive-fit connection between the securing element 3 and the tulip 202 after re-solidification of the thermoplastic material, said positive-fit connection being with respect to a translatory movement along the longitudinal axis of the fastener receiving opening 11 (of the inner thread 203, in the embodiment shown). In the exemplary embodiment shown, said structure is the inner tread 203 of the tulip 202.

The securing element 3 cannot be moved in the proximal direction after re-solidification of the thermoplastic material due to these positive-fit connections. Hence, the setscrew 2 cannot loosen after implantation of the implant system.

The exemplary embodiment of the securing element 3 shown in FIG. 56 includes the optional feature of having a shape that allows direct access to the proximal end of setscrew 2 (fastener) after re-solidification of the thermoplastic material. This allows for removal of the securing element 2, and hence of the implant system—by applying a torque to the setscrew 2 that is sufficient to break the securing element 2.

Alternatively to the securing element 3 and its mounting disclosed with respect to FIGS. 55 and 56, the securing element 3 (the thermoplastic material, as the case may be) and its mounting can be of the kind shown in FIGS. 5, 6, 19, 29, 32, 33, 52 and 53, for example.

Figure 57:
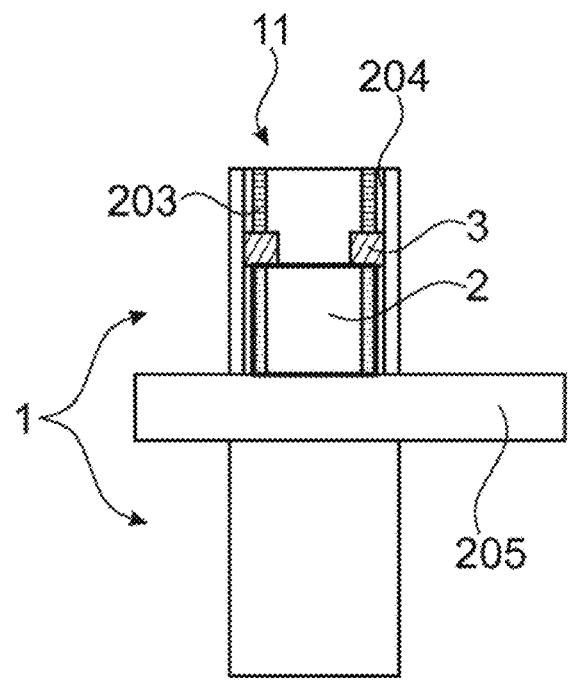

FIG. 57 shows schematically an implant system including an intramedullary rod 1 (intramedullary nail) and a locking screw 205.

In the embodiment shown, the intramedullary rod 1 includes an opening with an inner thread 203 and with the axial openings 204.

The intramedullary rod 1 can be considered as the implant part. The locking screw 205 can be considered as a second implant part.

In the embodiment shown, the locking screw 205 can be fixed relative to the intramedullary rod 1 by the use of the fastener being a locking bolt 2 and the securing element 3 in the same manner as disclosed with respect to FIGS. 55 and 56.

Alternatively to the securing element 3 and its mounting disclosed with respect to FIG. 57, the securing element 3 (the thermoplastic material, as the case may be) and its mounting can be of the kind shown in FIGS. 5-7, 19, 20, 23, 28, 29, 32, 33, 39, 46, 48, 52 and 53, for example.

Figure 58:
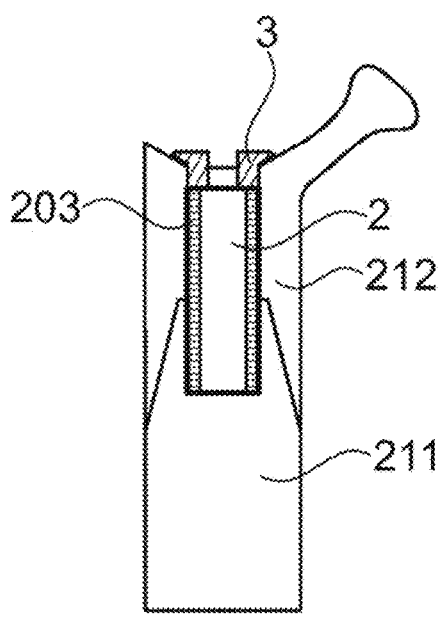

FIG. 58 shows schematically an implant system being a modular prosthesis. The exemplary modular prosthesis shown includes a head 212 and a stem 211. The head 212 and the stem 211 are separate parts before implantation.

In the embodiment shown, the head 212 and the stem 211 include an opening with an inner thread 203.

The head 212 can be considered as the implant part. The stem 211 can be considered as a second implant part.

In the embodiment shown, the head 212 and the stem 211 are connected to each other by a fastener being a tensioning screw 2 (turnbuckle, clamp screw). The tensioning screw 2 can be secured against a rotation relative to the head 212 and/or against an axial (back-out) movement by the securing element 3.

Again, the securing element 3 and its mounting can be alternatively of the kind shown in preceding.

FIGS. 59-63 show the application of the invention in an implant system being an osteosynthesis system including the implant part being a compression plate 1.

A compression plate is used whenever a first bone portion 213 and a second bone portion 214 need to be fixed relative to each other under compression, for example whenever a gap 220 needs to be closed in order to promote direct bone healing, for example.

In the embodiment shown in FIGS. 59-63 the gap 220 is caused by a fracture. However, the gap 220 can also be a joint space, for example. Further, the implant system can include an element being pushed into the gap 220, said element being compressed between the first and second bone portions, for example.

A compression plate can be fixed properly to the two bone portions only if at least one of the following applies during implantation procedure: A fastener (also called "load screw" in compression plate systems) can vary its angle relative to the compression plate, and the compression plate can move radially relative to the longitudinal axis of the load screw. However, this needed degree of freedom between the load screw and the compression plate make the use of additional fasteners (sometimes called "fixation screws" or additional load screes) mandatory. Otherwise, the load screw can (and normally will) untighten and hence the compression will be reduced which leads to a longer healing time and adversely affects direct bone healing.

In an implant system according to the invention, there is no need for the additional fasteners (the fixation screws). This means that there is also no need for additional bores in the bone portions. This also means that the implantation procedure is simplified.

If the implant system according to the invention is a compression plate system, the implant part 1 is the compression plate, the fastener 2 is the load screw and the thermoplastic material 3 (the securing element as the case may be) is the element of the implant system that makes the fixation screws redundant.

Figure 59:
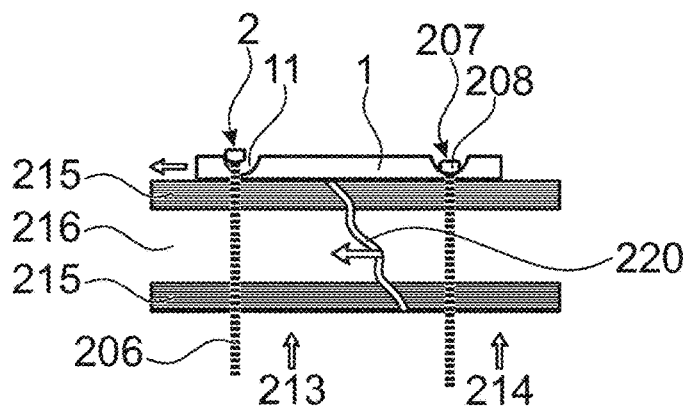
Figure 60:
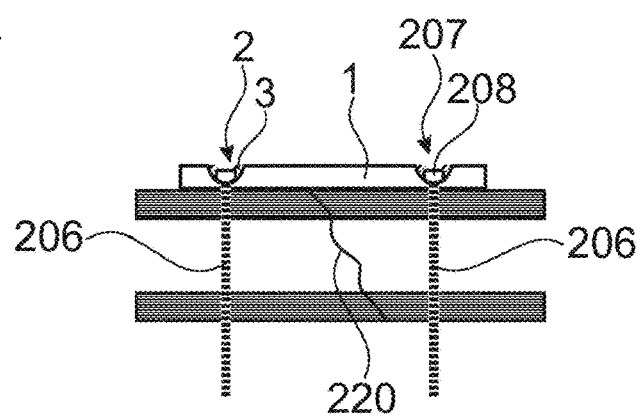

FIGS. 59 and 60 show exemplarily the simple case of a fracture that needs to be axially compressed only. In order to establish the axial compression the load screw 2 and the receiving opening 11 of the compression plate 1 need—in the shown exemplary case—to be designed for the compression plate 1 to move radially with respect to the longitudinal axis of load screw 2. In other words, the load screw 2 and the receiving opening 11 of the compression plate 1 need to be designed for the compression plate 1 to move along the longitudinal axis of the two bone portions during tightening of the load screw 2.

For example, the load screw 2 can include a screw head 208 having a diameter that increases in proximal direction and the receiving opening 11 can have a diameter that decreases in distal direction. Further, the receiving opening 11 can be designed in a manner that the load screw 2 can be inserted in a non-centric manner into the receiving opening 11. The receiving opening can have a non-round cross-section, for example an elliptic cross-section.

For example, in such a configuration, the inclined distal surface of the screw head 208 slides down the inclined surface of the receiving opening 11 as the load screw 2 is tightened. This causes said radial movement of the compression plate 1 with respect to the longitudinal axis of the load screw 2.

The radial movement of the compression plate 1 with respect to the longitudinal axis of the load screw 2 causes a movement of the second bone portion 214 relative to the first bone portion 213 that is along the longitudinal axis of the two bone portions if the load screw 2 is tightened in the first bone portion 213 and the compression plate 1 is anchored in the second bone portion 214, for example by a fixation screw 207, prior to the step of tightening the load screw 2. This movement of the second bone portion 214 closes the gap 220 between the two bone portions and put the two bone portions under axial compression.

In the embodiment shown, the load screw 2 and the fixation screw 207 have a screw shank 206 with a thread. However, one can envisage other kinds of fasteners, for example fasteners including thermoplastic material or screws including a screw shank that includes a first region with a thread and a second region without thread.

FIG. 59 shows the situation during tightening of the load screw 2.

Any untightening of the load screw 2, this means any movement of the load screw 2 relative to compression plate 1 reduces the compression. In particular, any axial (back-out) movement, any rotation of the load screw 2 relative to the compression plate and to the first bone portion 213, respectively, and any radial movement of the compression plate 1 relative to the longitudinal axis of the load screw 2 reduces the compression.

Such an untightening can be prevent by equipping the load screw 2, the compression plate 1 and the thermoplastic material 3 (the securing element as the case may be) accordingly. For example, the load screw 2, the compression plate 1 and the thermoplastic material 3 (the securing element as the case may be) can be equipped as shown in FIGS. 5-9, 19, 20, 28, 29, 32, 33, 39, 42, 46, 52 and 53.

FIG. 60 shows the load screw 2 secured exemplarily by a thermoplastic element 3 forming a cap. In the embodiment shown, the thermoplastic material is a hard thermoplastic material as discussed above.

Figure 61:
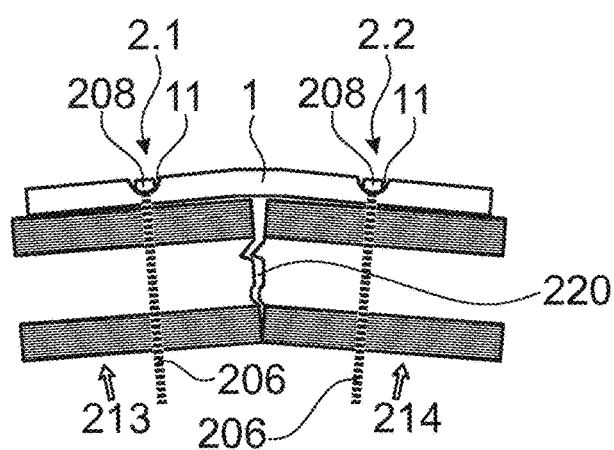
Figure 62:
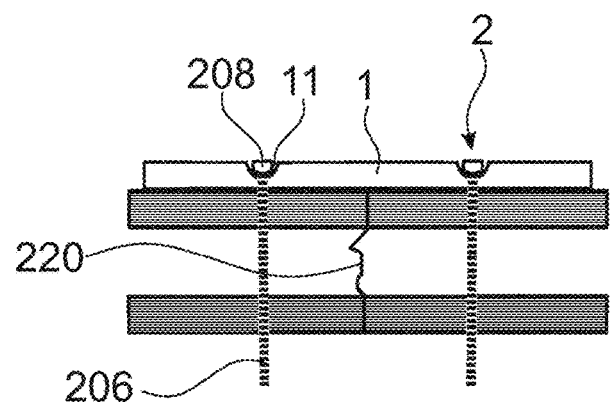
Figure 63:
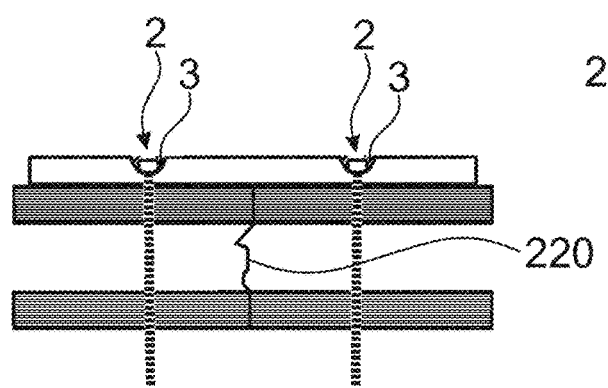

FIGS. 61-63 show exemplarily a rather simple medical case in which the first bone portion 213 and the second bone portion 214 need to be aligned relative to each other and compressed.

For example, the implant system can include a pre-bent compression plate 1, a first load screw 2.1 to be fixed in the first bone portion 213 and a second load screw 2.2 to be fixed in the second bone portion 214.

In the case of a pre-bent compression plate 1 that is deformed plastically for aligning and compressing the two bone portions during implantation procedure, the load screws and the receiving openings 11 of the compression plate 1 need be designed for the load screws to vary in angle relative to the compression plate 1. Otherwise, potentially damaging mechanical load is applied to the bone portions, in particular to the rather thin compact bone 215 and the spongy bone 216, and/or the compression plate 1 cannot be bent in a manner adapted to the aligned bone portions.

FIG. 61 shows the situation prior to tightening the loading screws.

FIG. 62 shows the situation after tightening the loading screws. The compression plate has deformed and caused the bone portions to align. Further, the bone portions are compressed. The compression can be established by the deformation of the compression plate 1. The compression can be caused or increased by the features shown in FIGS. 59-60.

Any untightening of a load screw 2, this means any movement of a load screw 2 relative to compression plate 1 reduces the compression. In particular, any axial (back-out) movement, any rotation of the load screw 2 relative to the compression plate and to the first bone portion 213, respectively, any variation of the angle of a load screw relative to the compression plate 1, and any radial movement of the compression plate 1 relative to the longitudinal axis of the load screw 2 reduces the compression.

Such an untightening can be prevent by equipping the load screws 2, the compression plate 1 and the thermoplastic material 3 (the securing element as the case may be) accordingly. For example, the load screws 2, the compression plate 1 and the thermoplastic material 3 (the securing element as the case may be) can be equipped as shown in FIGS. 5-9, 19, 20, 28, 29, 32, 33, 39-42, 43*a*, 44, 45*a*, 46, 47*b*, 48-54.

FIG. 63 shows the load screws 2 secured exemplarily by a thermoplastic element 3 forming a cap. In the embodiment shown, the thermoplastic material is a hard thermoplastic material as discussed above.

What is claimed is:

1. An implant system, comprising an implant part and at least one fastener, the implant part having, for the at least one fastener, a fastener receiving opening, the system further comprising thermoplastic material, the thermoplastic material being equipped for being liquefied by ultrasonic vibration and being an initially separate element or an element that is separable to be a separate element by applying a pressing or twisting force, wherein the at least one fastener, the implant part and the thermoplastic material are equipped for the thermoplastic material, after re-solidification, to secure the at least one fastener against at least one of an axial (back-out) movement of the at least one fastener, a rotation of the at least one fastener relative to the implant part, a variation of the angle of the at least one fastener relative to the implant part, and wherein the thermoplastic material is decoupled vibrationally from the implant part and the at least one fastener.

2. The implant system according to claim 1, wherein the at least one fastener and the implant part are equipped for the thermoplastic material, after re-solidification, to cause a connection between the at least one fastener and the implant part and wherein the connection secures the at least one fastener against at least one of the axial (back-out) movement of the at least one fastener, the rotation of the at least one fastener relative to the implant part, the variation of the angle of the at least one fastener relative to the implant part.

3. The implant system according to claim 1, comprising a securing element comprising the thermoplastic material, wherein the at least one fastener, the implant part and the securing element are equipped for the securing element, after re-solidification, to secure the at least one fastener against at least one of the axial (back-out) movement of the at least one fastener, the rotation of the at least one fastener relative to the implant part, the variation of the angle of the at least one fastener relative to the implant part.

4. The implant system according to claim 1, wherein the implant part is a fixation element, in particular a plate being shaped to be placed against human or animal bone tissue or a rod.

5. The implant system according to claim 1, wherein the implant part is a first implant part and the implant system comprises a second implant part, wherein the first implant part, the second implant part and the at least one fastener are equipped for the at least one fastener to fix the relative position of the first and second implant part.

6. The implant system according to claim 1, wherein the at least one fastener is arrangeable relative to the implant part to cause a clamping force to the implant part and wherein the thermoplastic material is designed to prevent after re-solidification a relative movement of the at least one fastener and the implant part that reduces the clamping force.

7. The implant system according to claim 1, wherein the at least one fastener is a screw comprising a thread.

8. The implant system according to claim 1, wherein the thermoplastic material is deformable to a first state and to a second state, wherein the thermoplastic material in the first state is able to secure the at least one fastener against axial (back-out) movement but not against variation of the angle of the at least one fastener relative to the implant part, and wherein the thermoplastic material in the second state is able to secure the at least one fastener against axial (back-out) movement and against variation of the angle of the at least one fastener relative to the implant part.

9. The implant system according to claim 1, wherein the thermoplastic material is designed to form a cap at a proximal end of the at least one fastener.

10. The implant system according to claim 9, wherein the at least one fastener, the implant part and the thermoplastic material are equipped for the thermoplastic material, after re-solidification, to be removable.

11. The implant system according to claim 1, wherein at least one of the at least one fastener, the thermoplastic material and the implant part comprises a guidance portion, wherein the guidance portion is designed for preventing ultrasonic vibration sufficient to liquefy the thermoplastic material to be coupled into the thermoplastic material.

12. The implant system according to claim 1, comprising a spacer equipped for preventing the coupling of ultrasonic vibration into the thermoplastic material after the thermoplastic material has been deformed into a predefined state.

13. The implant system according to claim 1, wherein the implant system comprises a securing element, wherein the at least one fastener receiving opening and the shape of the at least one fastener are designed to allow for a variation of the angle of the at least one fastener relative to the implant part, and wherein the securing element is equipped for allowing a variation of the angle of the at least one fastener relative to the implant part and for securing the at least one fastener against the axial (back-out) movement after re-solidification.

14. The implant system according to claim 13, wherein the securing element forms at least one of a stop and a rotation lock or wherein the securing element is equipped for deforming in a manner that it forms at least one of a stop and a rotation lock.

15. The implant system according to claim 13, wherein the securing element is equipped for allowing the variation of the angle of the at least one fastener relative to the implant part by being deformable.

16. The implant system according to claim 13, wherein the securing element is equipped for allowing the variation of the angle of the at least one fastener relative to the implant part in a first direction and for securing the at least one fastener against the variation of the angle of the at least one fastener relative to the implant part in a second direction.

17. The implant system according to claim 1, wherein the thermoplastic material fixes the orientation of the at least one fastener relative to the implant part with respect to all angles.

18. The implant system according to claim 1, wherein the at least one fastener or the fastener receiving opening has undercut structures for the thermoplastic material to flow into.

19. The implant system according to claim 1, wherein the at least one fastener has an insertion tool receiving structure with a non-circular cross section.

20. The implant system according to claim 1, wherein the fastener has a plurality of parts that are initially movable relative to each other and that during the process are fixable relative to each other.

21. The implant system according to claim 1, wherein the fastener receiving opening or a head of the at least one fastener has a non-round outer shape.

22. The implant system according to claim 1, wherein the at least one fastener includes a head having at least one through opening for a thermoplastic element to be inserted therethrough.

23. The implant system according to claim 1, wherein the implant part has a distally extending collar around the fastener receiving opening that enhances the depth along which the at least one fastener may engage.

24. The implant system according to claim 1, wherein the at least one fastener comprises a structure that is designed to direct liquefied thermoplastic material in a predefined direction.

25. The implant system according to claim 24, wherein the at least one fastener comprises a fastener head, wherein the structure that is designed to direct liquefied thermoplastic material is arranged on a proximal surface of the fastener head and wherein said structure is a channel, a groove or an undercut portion.

26. The implant system according to claim 24, wherein the thermoplastic material is designed to engage with the structure that is designed to direct liquefied thermoplastic material in a predefined direction and wherein said structure is designed to contribute to the securing of the at least one fastener against the axial (backout) movement of the fastener.

27. The implant system according to claim 1, wherein the thermoplastic material has a shape comprising at least one of:
  a protrusion that is designed to engage with a structure for the thermoplastic material to flow into;
  a bridge portion, a first protrusion and a second protrusion, wherein the first protrusion is designed to engage with a first structure for the thermoplastic material to flow into and the second protrusion is designed to engage with a second structure for the thermoplastic material to flow into, wherein the first structure is arranged at the implant part and the second structure is arranged at the at least one fastener.

28. The implant system according to claim 1, wherein the implant part comprises the thermoplastic material and wherein the thermoplastic material is arranged to form a proximal portion of the fastener receiving opening.

29. A method of implanting an implant system, especially according to claim 1, the method comprising the steps of: placing the implant part relative to the bone tissue or another implant part; anchoring the at least one fastener in the bone tissue or in the other implant part; causing ultrasonic vibration energy to impinge on thermoplastic material until a flow portion thereof becomes flowable and flows relative to the implant part and the at least one fastener; stopping the energy transfer; and causing the thermoplastic material to re-solidify, whereby the at least one fastener is secured against at least one of an axial (back-out) movement, a rotation relative to the implant part, a variation of the angle of the at least one fastener relative to the implant part, wherein the thermoplastic material is decoupled vibrationally from the implant part and the at least one fastener.

30. The method according to claim 29, wherein an angular orientation of the at least one fastener relative to the implant part is fixed by the thermoplastic material.

31. The method according to claim 29, comprising the step of clamping the implant part between the at least one fastener and the bone tissue or the other implant part, wherein the thermoplastic material is designed to prevent after re-solidification a relative movement of the at least one fastener and the implant part that reduces the clamping force.

32. The method according to claim 29, wherein the implant system comprises the securing element and wherein the at least one fastener, the implant part and the securing element are formed to allow for a variation of the angle of the at least one fastener relative to the implant part after implantation.

33. The method according to claim 29, comprising the step of forming a cap at a proximal end of the at least one fastener.

34. The method according to claim 29, comprising the step of removing the thermoplastic material by applying a torque to a proximal end of the at least one fastener.

35. The method according to claim 29, comprising the step of guiding at least one of the at least one fastener and the thermoplastic material by a tool comprising a guide portion.

* * * * *